(12) United States Patent
Dunson, Jr. et al.

(10) Patent No.: US 7,781,191 B2
(45) Date of Patent: Aug. 24, 2010

(54) TREATMENT OF BIOMASS TO OBTAIN A TARGET CHEMICAL

(75) Inventors: James B. Dunson, Jr., Newark, DE (US); Melvin P. Tucker, III, Lakewood, CO (US); Richard T. Elander, Evergreen, CO (US); Susan Marie Hennessey, Avondale, PA (US)

(73) Assignees: E. I. du Pont de Nemours and Company, Wilmington, DE (US); Alliance For Sustainable Energy LLC, Golden, CO (US)

( * ) Notice: Subject to any disclaimer, the term of this patent is extended or adjusted under 35 U.S.C. 154(b) by 0 days.

(21) Appl. No.: 11/403,087

(22) Filed: Apr. 12, 2006

(65) Prior Publication Data

US 2007/0031919 A1 Feb. 8, 2007

Related U.S. Application Data

(60) Provisional application No. 60/670,437, filed on Apr. 12, 2005.

(51) Int. Cl.
*C12P 7/00* (2006.01)
*C12P 19/00* (2006.01)
*C12P 19/14* (2006.01)

(52) U.S. Cl. .............. 435/99; 435/41; 435/72; 435/105; 435/161; 426/7

(58) Field of Classification Search .......... 435/41, 435/72, 99, 105, 161; 426/7
See application file for complete search history.

(56) References Cited

U.S. PATENT DOCUMENTS

| | | | |
|---|---|---|---|
| 4,136,207 A | 1/1979 | Bender | |
| 4,186,658 A | 2/1980 | Brown | |
| 4,461,648 A | 7/1984 | Foody | |
| 4,859,283 A | 8/1989 | Jayawant | |
| 5,008,473 A | 4/1991 | Breitkopf et al. | |
| 5,037,663 A | 8/1991 | Dale | |
| 5,192,673 A | 3/1993 | Jain et al. | |
| 5,356,812 A | 10/1994 | Matsuyama et al. | |
| 5,366,553 A | 11/1994 | Lair et al. | |
| 5,705,369 A | 1/1998 | Torget et al. | |
| 5,747,320 A * | 5/1998 | Saha et al. | 435/209 |
| 5,879,463 A | 3/1999 | Proenca | |
| 5,916,780 A | 6/1999 | Foody et al. | |
| 6,013,494 A | 1/2000 | Nakamura et al. | |
| 6,090,595 A | 7/2000 | Foody et al. | |
| 6,159,738 A | 12/2000 | Donnelly et al. | |
| 6,176,176 B1 | 1/2001 | Dale et al. | |
| 6,228,630 B1 | 5/2001 | Kofod et al. | |
| 6,254,914 B1 | 7/2001 | Singh et al. | |
| 6,358,716 B1 | 3/2002 | Bulthuis et al. | |
| 6,358,717 B1 | 3/2002 | Blaschek et al. | |
| 6,514,733 B1 | 2/2003 | Emptage et al. | |
| 6,777,207 B2 | 8/2004 | Kjeldsen et al. | |
| 6,861,237 B2 | 3/2005 | Anderson et al. | |
| 6,962,805 B2 | 11/2005 | Asakura et al. | |
| 2003/0162271 A1 | 8/2003 | Zhang et al. | |
| 2003/0170834 A1 | 9/2003 | Gatenby et al. | |
| 2004/0016525 A1 | 1/2004 | Gervais | |
| 2004/0231060 A1 | 11/2004 | Burdette et al. | |
| 2005/0161038 A1 | 7/2005 | Pinatti et al. | |
| 2005/0250192 A1 | 11/2005 | Shanmugam et al. | |
| 2006/0003429 A1 | 1/2006 | Forst et al. | |
| 2007/0031918 A1 | 2/2007 | Dunson et al. | |
| 2008/0187973 A1 | 8/2008 | Viitanen et al. | |
| 2008/0286870 A1 | 11/2008 | Viitanen et al. | |

FOREIGN PATENT DOCUMENTS

| | | |
|---|---|---|
| EP | 0263515 A2 | 4/1988 |
| EP | 0332234 B1 | 9/1989 |
| EP | 136359 B1 | 4/1994 |
| FR | 656385 | 5/1929 |
| JP | 47004505 | 3/1972 |
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56010035 | 2/1981 |
| JP | 57150381 | 9/1982 |
| JP | 623776 | 1/1987 |
| JP | 1003581 | 1/1989 |
| JP | 3207079 | 9/1991 |
| JP | 450572 | 2/1992 |
| JP | 859681 | 3/1996 |
| JP | 3723579 | 9/2005 |

(Continued)

OTHER PUBLICATIONS

Mosier et al. 2005. Features of promising technologies for pretreatment of lignocellulosic biomass. Bioresource Technology 96 (2005) 673-686.*

(Continued)

*Primary Examiner*—Taeyoon Kim

(57) ABSTRACT

Target chemicals were produced using biocatalysts that are able to ferment sugars derived from treated biomass. Sugars were obtained by pretreating biomass under conditions of high solids and low ammonia concentration, followed by saccharification.

35 Claims, 1 Drawing Sheet

FOREIGN PATENT DOCUMENTS

| | | | |
|---|---|---|---|
| JP | 3899572 | | 1/2007 |
| KR | 2001-0048482 | * | 6/2001 |
| WO | 94/03646 A1 | | 2/1994 |
| WO | 03/078644 A2 | | 9/2003 |
| WO | 2004/018645 A2 | | 3/2004 |
| WO | 2004/081185 A1 | | 9/2004 |
| WO | 2007/041269 A2 | | 4/2007 |
| WO | 2007/050671 A2 | | 5/2007 |

OTHER PUBLICATIONS

Sun et al. 2002.Hydrolysis of lignocellulosic materials for ethanol production: a review. Bioresource Technology 83 (2002) 1-11.*
Curreli et al., Complete and Efficient Enzymic Hydrolysis of Pretreated Wheat Straw, Process Biochem., 2002, vol. 37:937-941.
Teymouri et al., Optimization of the Ammonia Fiber Expolsion (AFEX) Treatment Parameters for Enzymatic Hydrolysis of Corn Stover, Bioresource Tech., 2005, vol. 96:2014-2018.
Barron et al., Ethanol Production by Kluyveromyces Marxianus IMB3 During Growth on Straw-Supplemented Whiskey Distillery Spent Wash at 45 Degrees C., Bioprocess Engineering, 1997, vol. 17:383-386.
Kim et al., Pretreatment of Corn Stover by Soakingin Aqueous Ammonia, Applied Biochemistry and Biotechnology, 2005. vol. 121-124:p. 1119-1132.
Aden et al., Biofuels for Sustainable Transportation , National Renewable Energy Laboratory Report TP-510-32438, 2000.
Lloyd et al., Application of a Depolymerization Model for Predicting Thermochemical Hydrolysis of Hemicellulose, Appl. Biochem. & Biotechnol., 2003, vol. 105:53-57.
Lloyd et al., Combined Sugar Yields for Dilute Sulfuric Acid Pretreatment of Corn Stover Followed by Enzymatic Hydrolysis of the Remaining Solids, Bioresource Technology, 2005, vol. 96:1967-1977.
Gusakov et al., Kinetics of the Enzymatic Hydrolysis of Cellulose: 1. Mathematical for a Batch Reactor Process, Enz. Microb. Technol., 1985, vol. 7:346-352.
Lee et al., Cellulose Hydrolysis Under Extremely Low Sulfuric Acid and High Temperature Conditions, Appl. Biochem. Biotech., 2001, vol. 91:331-340.
Gusakov et al., Enhancement of Enzymatic Cellulose Hydrolysis Using a Novel Type of Bioreactor With Intensive Stirring Induced by Electromagnetic Field, Appl. Biochem. Biotechnol., 1996, vol. 58:141-153.
International Search Report Dated Aug. 16, 2007, International Application No. PCT/US/2006/014020, International Filing Date: Apr. 12, 2006, 4 Pages.
Yamadaya et al., Hydrocracking of Tetralin on Supported Nicke-Tungsten Catalysts, Bulletin of the Chemical Society of Japan, 1977, vol. 50:79-87.
U.S. Appl. No. 11/402,757, filed Apr. 12, 2006, James B. Dunson et al.
U.S. Appl. No. 11/741,892, filed Apr. 30, 2007, Gail K. Donaldson et al.
U.S. Appl. No. 11/741,916, filed Apr. 30, 2007, Gail K. Donaldson et al.
U.S. Appl. No. 11/402,464, filed Feb. 8, 2007, James B. Dunson et al.
Gould, Alkaline Peroxide Delignification of Agricultural Residues to Enhance Enzymatic Saccharification, Biotech. and Bioengr., 1984, vol. 26:46-52.
Teixeira et. al., Alkaline and Peracetic Acid Pretreatments of Biomass for Ethanol Production, Appl. Biochem. and Biotech., 1999, vol. 77-79:19-34.
Elshafei et. al., The Saccharification of Corn Stover by Cellulase From *Penicillium funiculosum*, Bioresource Tech., 1991, vol. 35:73-80.
Kim et. al., Pretreatment and Fractionation of Corn Stover by Ammonia Recycle Percolation Process, Biosesourse Technology, 2005, vol. 96:2007-2013.
Lynd et. al., Microbial Cellulose Utilization: Fundamentals and Biotechnology, Microbiol. Mol. Biol. Rev., 2002, vol. 66:506-577.
Eur. J. Biochem., Nomenclature Committee of the International Union of Biochemistry and Molecular Biology, Supplement: Corrections and Additions, 1994, vol. 223:1-5.
Eur. J. Biochem., Nomenclature Committee of the International Union of Biochemistry and Molecular Biology, Supplement 2: Corrections and Additions, 1995, vol. 232:1-6.
Eur J. Biochem., Nomenclature Committee of the Internationa Union of Biochemistry and Molecular Biology, Supplement 3: Corrections and Additions, 1996, vol. 237:1-5.
Eur. J. Biochem., Nomenclature Committee of the International Union of Biochemistry and Molecular Biology, Supplement 4: Corrections and Additions, 1997, vol. 250:1-6.
Eur. J. Biochem., Nomenclature of the International Union of Biochemistry and Molecular Biology, Enzyme Supplement 5, 1999, vol. 264:610-650.
Miller et. al., Use of Dinitrosalicylic Acid Reagent for Determination of Reducing Sugar, Anal. Chem., 1959, vol. 31:426-428.
Jones et. al., Acetone-Butanol Fermentation Revisted, Microbiol. Rev., 1986, vol. 50:484-524.
Underwood et. al., Genetic Changes to Optimize Carbon Printing Between Ethanol and Biosynthesis in *Ethanologenic coli*, Appl. Environ. Microbiol., 2002, vol. 68:6263-6272.
Zhou et. al., Production of Optically Pure D-Lactic Acid in Mineral Salts Medium by Metabolically Engineered *Escherichia coli* W3110, Appl. Environ. Microbiol., 2003, vol. 69:399-407.
Tay et. al., Production of L (+)-Lactic Acid From Glucose and Starch by Immobilized Cells of Rhizopus Oryzae in a Rotating Fibrous Bed Bioreactor, 2002, vol. 80:1-12.
Niu et. al., Benzene-Free Synthesis of Adipic Acid, Biotechnol. Prog., 2002, vol. 18:201-211.
Cheryan et. al., Production of Acetic Acid by *Clostridium thermoaceticum*, Adv. Appl. Microbiol. 1997, vol. 43:1-33.
Freer, Acetic Acid Production by Dekkera/Brettanomyces Yeasts, World Journal of Microbiology & Biotechnology, 2002, vol. 18:271-275.
Lin et. al., Metabolic Engineering of Aerobic Succinate Production Systems in *Esherichia coli* to Improve Process Productivity and Achieve the Maximum Theorectical Succinate Yield, Metab. Eng., 2005, vol. 7:116-127.
Li et. al., Efficient Pyruvate Production by a Multi-Vitamin Auxotroph of *Torulopsis glabrata*: Key Role Optimization of Vitamin Levels, Appl. Microbiol. Technol., 2001, vol. 55:680-685.
Yokota et. al., Pyruvic Acid Production by an F1-ATPase-Defective Mutant of *Escherichia coli* W1485lip2, Biosci. Biotech. Biochem., 1994, vol. 58:2164-2167.
Suwannakham et. al., Enhanced Propionic Acid Fermentation by Propionibacterium Acidipropionici Mutant Obtained by Adaptation in a Fibrous-Bed Bioreactor, Biotechnol. Bioeng.,2005, vol. 91:325-337.
Wu et. al., Extractive Fermentation for Butyric Acid Production From Glucose by *Clostridium tyrobutyricum*, 2003, vol. 82:93-102.
Janssen, Propanol as an End Product of Theronine Fermentation, Arch. Microbiol., 2004, vol. 182:482-486.
Anastassiadis et. al., Process Optimization of Continuous Gluconic Acid Fermentation by Isolated Yeast-Like Strains of *Aureobasidium pullulans*, Biotechnol. Bioeng., 2005, vol. 91:494-501.
Singh et. al., Optimisation of Fermentation Conditions for Gluconic Acid Production by a Mutant of *Aspergillus niger*, Indian J. Exp. Biol., 2001, vol. 39:1136-1143.
Elfari et. al., Applied Genetics and Molecular Biotechnology, Appl. Microbiol. Biotech., 2005, vol. 66:668-674.
Reddy et. al., Enhanced Production of Itaconic Acid From Corn Starch and Market Refuse Fruits by Genetically Manipulated *Aspergillus terreus* SKR10, Bioresour. Technol., 2002, vol. 85:69-71.
Ui-Haq et. al., Optimization of Nitrogen for Enhanced Citric Acid Productivity by a 2-Deoxy D-Glucose Resistant Culture of *Aspergilluis niger* NG-280, Bioresour. Technol., 2005, vol. 96:645-648.
Mussatto et. al., Xylitol Production From High Xylose Concentration: Evaluation of the Fermentation in Bioreactor Under Different Stirring Rates, J. Appl. Microbiol., 2003, vol. 95:331-337.
Gorenflo et. al., Development of a Process for the Biotechnological Large-Scale Production of 4-Hydroxyvalerate-Containing Polyesters and Characterization of Their Physical and Mechanical Properties, Biomacromolecules, 2001, vol. 2:45-57.

Ui et. al., Production of L-2-3-Butanediol by a New Pathway Constructed in *Escherichia coli*, Lett. Appl. Microbiol., 2004, vol. 39:533-537.

Okamoto et. al., Development of an Industrially Stable Process for the L-Theronine Fermentation by an L-Methionine-Auxotrophic Mutant of *Escherichia coli*, J. Biosci. Bioeng., 2000, vol. 89:87-89.

Kumar et. al., Effect of Cysteine on Methionine Production by a Regulatory Mutant of *Corynebacterium lilium*, Bioresour. Technol., 2005, vol. 96:287-294.

Durre, New Insights and Novel Developments in Clostridial Acetone/Butanol/Isopropanol Fermentation, Appl. Microbiol. Biotechnol., 1998, vol. 49:639-648.

Groot et. al., Technologies for Butanol Recovery Intergrated With Fermentations, Process. Biochem., 1992, vol. 27:61-75.

K. N. Joblin et. al., Fermentation of Barley Straw by Anaerobic Rumen Bacteria and Fungi in Axenic Culture and in Co-Culture With Methanogens, Letters in Applied Microbiology, 1989, vol. 9:195-197.

Kurakake et. al., Pretreatment With Ammonia Water for Enzymatic Hydrolysis of Corn Husk, Bagasse, and Switchgrass, Appiled Biochemistry and Biotechnology, 2001, vol. 90:251-259.

Taylor et. al., Corn Milling Pretreatment With Anhydrous Ammonia, Applied Biochemistry and Biotechnology, 2003, vol. 104:141-148.

Cao et. al., Production of 2, 3 Butanediol From Pretreated Corn Cob by *Klebsiella oxytoco* in the Presence of Fungal Cellulase, Applied Biochemistryand Biotechnology, 1997, vol. 63-65:129-139.

Cao et. al., Ethanol Production From Corn Cob Pretreated by the Ammonia Steeping Process Using Genetically Engineered Yeast, Biotechnology Letters, 1996, vol. 18:1013-1018.

Iyer et. al., Ammonia Recycled Percolation Process for Pretreatment of Herbaceous Biomass, Applied Biochemistry and Biotechnology, 1996, vol. 57-58:121-132.

D. Ben-Ghedalia et. al., The Effect of Chemical Pretreatments and Subsequent Enzymatic Treatments on the Organic Matter Digestibility in Vitro of Wheat Straw, Nutrition Reports International, 1979, vol. 19:499-505.

A.C. Waiss et. al., Improving Digestibility of Straws for Ruminant Feed by Aqueous Ammonia, Journal of Animal Science, 1972, vol. 35:109-112.

Mosier et. al., Features of Promising Technologies for Treatment of Lignocellulosic Biomass, Bioresource Technology, 2005, vol. 96:673-686.

Nakayama et al., Fermentative Production of L-Arginine, ARG. Biol. Chem., 1972, vol. 36:675-1684.

Ryu et al., Bioconversion of Waste Cellulose by Using an Attrition Bioreactor, Biotechnol. Bioeng., 1983, vol. 25:53-65.

U.S. Appl. No. 11/403,087, filed Apr. 12, 2006, James B. Dunson et al.

Curreli et al., Complete and Efficient Enzymic Hydrolysis of Pretreated Wheat Straw, Process Biochem., 2002, vol. 37:937-941.

Teymouri et al., Optimization of the Ammonia Fiber Expolsion (AFEX) Treatment Parameters for Enzymatic Hydrolysis of Corn Stover, Bioresource Tech, 2005, vol. 96:2014-2018.

Barron et al., Ethanol Production by Kluyveromyces Marxianus IMB3 During Growth on Straw-Supplemented Whiskey Distillery Spent Wash At 45 Degrees C'., Bioprocess Engineering, 1997, vol. 17:383-386.

H. Hagino, Control Mechanisms in Aromatic Amino Acid Biosynthesis and the Amino Biosynthesis and the Amino Acid Production, Arg. Chem. Soc., Japan, 1976, vol. 50:R79-R87.

Aden et al., Biofuels for Sustainable Transportation, National Renewable Energy Laboratory Report TP-510-32438, 2000.

Lloyd et al., Application of a Depolymerization Model for Predicting Thermochemical Hydrolysis OH Hemicellulose, Appl. Biochem. & Biotechnol., 2003, vol. 105:53-67.

Lloyd et al., Combined Sugar Yields for Dilute Sulfuric Acid Pretreatment of Corn Stover Followed by Enzymatic Hydrolysis of the Remaining Solids, Bioresource Technol., 2005, vol. 96:1967-1977.

Gusakov et al., Kinetics of the Enzymatic Hydrolysis of Cellulose: 1. A Mathematical Model for a Batch Reactor Process, Enz. Microb. Technol., 1985, vol. 7:346-352.

Lee et al., Cellulose Hydrolysis Under Extremly Low Sulfuric Acid and High Temperature Conditions, Appl. Biochem. Biotech., 2001, vol. 91:331-340.

Gusakov et al., Enhancement Enzymatic Cellulose Hydrolysis Using a Novel Type of Bioreactor With Intensive Stirring Induced by Electromagnetic Field, Appl. Biochem. Biotechnol., 1996, vol. 58:141-153.

Kim et al., Pretreatment of Corn Stover by Soakingin Aqueous Ammonia, Applied and Biochemsitry and Biotechnology, 2005, vol. 121:1119-1131.

Hagino, Control Mechanisms in Aromatic Amino Acid Biosynthesis and the Amino Acid Production, Arg. Chem. Soc., Japan, 1976, vol. 50:R79-R87 (#5 of IDS filed Apr. 15, 2008.

Lin et al., Chemical Engineer's Handbook, 5th Edition, 1973, Chapter 4, McGraw-Hill, NY (#46 of IDS filed Apr. 15, 2008).

Perry et al., Chemical Engineer's Handbook, 5th Edition, Chapter 4, 1973 (#47 of IDS filed Apr. 15, 2008).

Kirk-Othmer Encyclopedia of Chemical Technology, 4th Edition, 1997 (#49 of IDS filed Apr. 15, 2008).

Teymouri, Farzaneh et al., Optimization of the ammonia fiber explosion (AFEX) treatment parameters for enzymatic hydrolysis of corn stover, Bioresource Technology, 2005, pp. 2014-2018, vol. 96, Elsevier Ltd.

Kim, Tae Hyun et al., Fractionation of corn stover by hot-water and aqueous ammonia treatment, Bioresource Technology, 2006, pp. 224-232, vol. 97, Elsevier Ltd.

\* cited by examiner

TREATMENT OF BIOMASS TO OBTAIN A TARGET CHEMICAL

This application claims the benefit of U.S. Provisional Application No. 60/670,437, filed Apr. 12, 2005.

STATEMENT OF GOVERNMENT RIGHTS

This invention was made with United States government support under Contract No. 04-03-CA-70224 awarded by the Department of Energy. The government has certain rights in this invention.

FIELD OF THE INVENTION

Methods for producing target chemicals using fermentable sugars derived from treating biomass are provided. Specifically, sugars obtained by pretreating biomass under conditions of high solids and low ammonia concentration, followed by saccharification, are used in fermentation by biocatalysts producing target chemicals.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products.

Pretreatment methods are used to make the carbohydrate polymers of cellulosic and lignocellulosic materials more readily available to saccharification enzymes. Standard pretreatment methods have historically utilized primarily strong acids at high temperatures; however due to high energy costs, high equipment costs, high pretreatment catalyst recovery costs and incompatibility with saccharification enzymes, alternative methods are being developed, such as enzymatic pretreatment, or the use of acid or base at milder temperatures where decreased hydrolysis of biomass carbohydrate polymers occurs during pretreatment, requiring improved enzyme systems to saccharify both cellulose and hemicellulose.

A number of pretreatment methods utilizing base have been proposed. Gould (Biotech. and Bioengr. (1984) 26:46-52) discloses a pretreatment method for lignocellulosic biomass using hydrogen peroxide ($H_2O_2$). The treatment is most efficient using $H_2O_2$ in an amount of at least 0.25 wt/wt with respect to substrate.

Teixeira, L., et al. (Appl. Biochem. and Biotech. (1999) 77-79:19-34) disclosed a series of biomass pretreatments using stoichiometric amounts of sodium hydroxide and ammonium hydroxide, with very low biomass concentration. The ratio of solution to biomass is 14:1.

Elshafei, A. et al. (Bioresource Tech. (1991) 35:73-80) examined the pretreatment of corn stover utilizing NaOH.

Kim, T. and Y. Lee (Bioresource Technology (2005) 96:2007-2013) report the use of high amounts of aqueous ammonia for the pretreatment of corn stover.

Patent Application WO2004/081185 discusses methods for hydrolyzing lignocellulose, comprising contacting the lignocellulose with a chemical; the chemical may be a base, such as sodium carbonate or potassium hydroxide, at a pH of about 9 to about 14, under moderate conditions of temperature, pressure and pH.

U.S. Pat. Nos. 5,916,780 and 6,090,595, describe a pretreatment process wherein a specified ratio of arabinoxylan to total nonstarch polysaccharides (AX/NSP) is assessed and used to select the feedstock.

In order to be an economically competitive process, a commercial process for the production of chemicals from a renewable resource biomass requires the hydrolysis of carbohydrates in lignocellulosic biomass to provide high yields of sugars at high concentrations, using low amounts of chemicals, to produce a source of fermentable sugars with low toxicity that are used by biocatalysts that produce value-added target chemicals.

SUMMARY OF THE INVENTION

The present invention provides methods for producing target chemicals that make use of biomass. The process of the invention involves pretreatment of biomass, at relatively high concentration, with a low concentration of ammonia relative to the dry weight of biomass. Following pretreatment, the biomass is treated with a saccharification enzyme consortium to produce fermentable sugars. The sugars are then contacted with a biocatalyst that can ferment the sugars and produce a target chemical. In one embodiment of the invention, the method comprises:
 a) contacting biomass with an aqueous solution comprising ammonia, wherein the ammonia is present at a concentration at least sufficient to maintain alkaline pH of the biomass-aqueous ammonia mixture but wherein said ammonia is present at less than about 12 weight percent relative to dry weight of biomass, and further wherein the dry weight of biomass is at a high solids concentration of at least about 15 weight percent relative to the weight of the biomass-aqueous ammonia mixture;
 b) contacting the product of step (a) with a saccharification enzyme consortium under suitable conditions to produce fermentable sugars; and
 c) contacting the product of step b) with at least one biocatalyst able to ferment the sugars to produce the target chemical under suitable fermentation conditions.

DETAILED DESCRIPTION OF THE INVENTION

Figure 1:
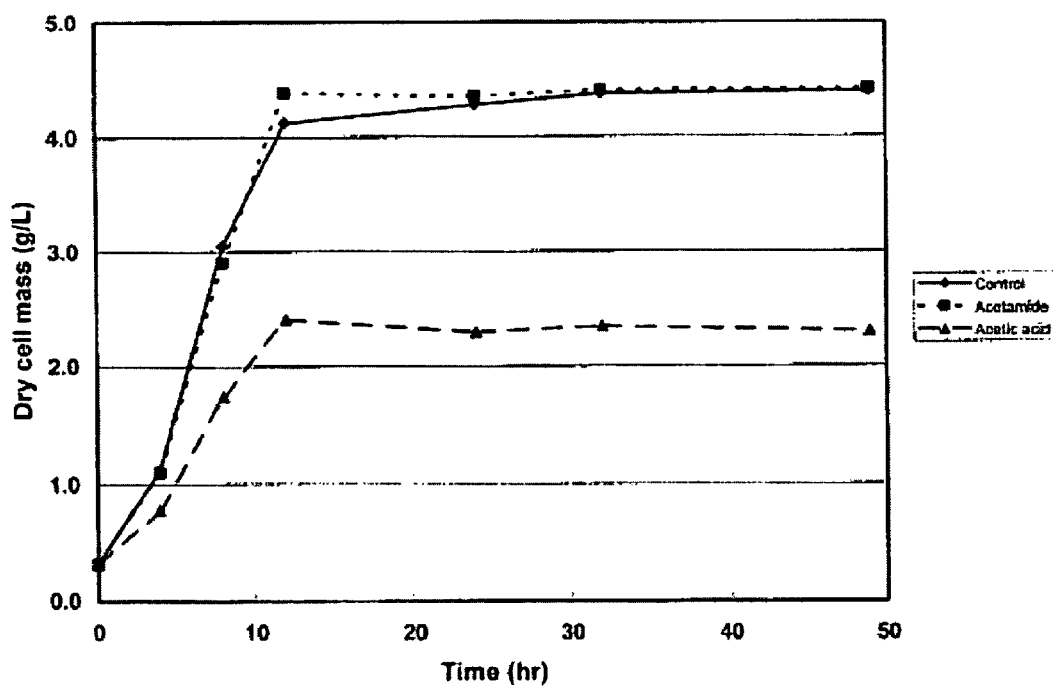
FIG. 1 shows the growth of *Zymomonas mobilis* 8b (described in US Patent Application Publication 2003/0162271 A1, examples IV, VI and XII) in the presence or absence of acetamide and acetic acid.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides methods for producing target chemicals that make use of biomass in the following manner: sugars are derived from biomass, which are then used as a carbon source for the growth of microorganisms that can make target chemicals as products of their metabolism. The sugars are released from the biomass by pretreating the biomass, at relatively high concentration, with a relatively low concentration of ammonia relative to the dry weight of the biomass. The ammonia-treated biomass is then digested with a saccharification enzyme consortium to produce fermentable sugars. The sugars are used as a fermentation substrate for growth of a microorganism, or biocatalyst, that is able to produce a target chemical.

DEFINITIONS

In this disclosure, a number of terms are used. The following definitions are provided:

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

The term "target chemical" refers to a chemical produced by fermentation. Chemical is used in a broad sense and includes molecules such as proteins, including, for example, peptides, enzymes and antibodies.

A target chemical that is "derivable from biomass" is a target chemical produced by a process whereby biomass is hydrolyzed to release fermentable sugars, and the fermentable sugars are fermented using at least one biocatalyst to produce a desired target chemical.

The terms "plasticizer" and "softening agent" refer to materials that cause a reduction in the cohesive intermolecular forces along or between polymer chains. Such materials may act, for example, to decrease crystallinity, or disrupt bonds between lignin and non-lignin carbohydrate fibers (e.g., cellulose or hemicellulose).

The term "saccharification" refers to the production of fermentable sugars from polysaccharides.

"Suitable conditions to produce fermentable sugars" refers to conditions such as pH, composition of medium, and temperature under which saccharification enzymes are active.

"Suitable fermentation conditions" refers to conditions that support the growth and target chemical production by a biocatalyst. Such conditions may include pH, nutrients and other medium components, temperature, atmosphere, and other factors.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the present method, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, fruits, flowers and animal manure. In one embodiment, biomass that is useful for the present method includes biomass that has a relatively high carbohydrate value, is relatively dense, and/or is relatively easy to collect, transport, store and/or handle. In one embodiment of the invention, biomass that is useful includes corn cobs, corn stover and sugar cane bagasse.

For the purposes of this invention, an "aqueous solution comprising ammonia" refers to the use of ammonia gas ($NH_3$), compounds comprising ammonium ions ($NH_4^+$) such as ammonium hydroxide or ammonium sulfate, compounds that release ammonia upon degradation such as urea, and combinations thereof in an aqueous medium.

The concentration of ammonia used in the present method is minimally a concentration that is sufficient to maintain the pH of the biomass-aqueous ammonia mixture alkaline and maximally less than about 12 weight percent relative to dry weight of biomass. This low concentration of ammonia is sufficient for pretreatment, and the low concentration may also be less than about 10 weight percent relative to dry weight of biomass. A very low concentration of 6 percent ammonia relative to dry weight of biomass, or less, also may be used for pretreatment. By alkaline is meant a pH of greater than 7.0. Particularly suitable is a pH of the biomass-aqueous ammonia mixture that is greater than 8. In one embodiment, ammonia is present at less than about 10 weight percent relative to dry weight of biomass. Particularly suitable is ammonia at less than about 6 weight percent relative to dry weight of biomass.

Ammonia as used in the present process provides advantages over other bases. Ammonia partitions into a liquid phase and vapor phase. Gaseous ammonia can diffuse more easily through biomass than a liquid base, resulting in more efficacious pretreatment at lower concentrations. Ammonia also is shown herein in Example 11 to compete with hydrolysis, via ammonolysis, of acetyl esters in biomass to form acetamide. Acetamide is less toxic than acetate to certain fermentation organisms, such as *Zymomonas mobilis* (as demonstrated herein in Example 12). Thus conversion of acetyl esters to acetamide rather than to acetic acid reduces the need to remove acetic acid. The use of ammonia also reduces the requirement to supplement growth medium used during fermentation with a nitrogen source. In addition, ammonia is a low-cost material and thus provides an economical process. Ammonia can also be recycled to the pretreatment reactor during pretreatment or following pretreatment, thus enabling a more economical process. For example, following pretreatment, as the temperature is decreased to that suitable for saccharification, ammonia gas may be released, optionally in the presence of a vacuum, and may be recycled. In a continuous process, ammonia may be continuously recycled.

According to the present method, the aqueous solution comprising ammonia may optionally comprise at least one additional base, such as sodium hydroxide, sodium carbonate, potassium hydroxide, potassium carbonate, calcium hydroxide and calcium carbonate. The at least one additional base may be added in an amount that is combined with ammonium to form an amount of total base that is less than about 20 weight percent relative to dry weight of biomass. Preferably the total second base plus ammonia is in an amount that is less than about 15 weight percent. Additional base(s) may be utilized, for example, to neutralize acids in biomass, to provide metal ions for the saccharification enzymes, or to provide metal ions for the fermentation growth medium.

In the present method, the dry weight of biomass is at an initial concentration of at least about 15% up to about 80% of the weight of the biomass-aqueous ammonia mixture. More suitably, the dry weight of biomass is at a concentration of from about 15% to about 60% of the weight of the biomass-aqueous ammonia mixture. The percent of biomass in the biomass-aqueous ammonia mixture is kept high to minimize the need for concentration of sugars resulting from saccharification of the pretreated biomass, for use in fermentation. The high biomass concentration also reduces the total volume of pretreatment material, making the process more economical.

The biomass may be used directly as obtained from the source, or energy may be applied to the biomass to reduce the size, increase the exposed surface area, and/or increase the availability of cellulose, hemicellulose, and/or oligosaccharides present in the biomass to ammonia and to saccharification enzymes used in the second step of the method. Energy means useful for reducing the size, increasing the exposed surface area, and/or increasing the availability of cellulose, hemicellulose, and/or oligosaccharides present in the biomass to ammonia and to saccharification enzymes include, but are not limited to, milling, crushing, grinding, shredding, chopping, disc refining, ultrasound, and microwave. This application of energy may occur before or during pretreatment, before or during saccharification, or any combination thereof.

Pretreatment of biomass with ammonia solution is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and a steam gun reactor (described in General Methods; Autoclave Engineers, Erie, Pa.). Much larger scale reactors with similar capabilities may be used. Alternatively, the biomass and ammonia solution may be combined in one vessel, then transferred to another reactor. Also biomass may be pretreated in one vessel, then further processed in another reactor such as a steam gun reactor (described in General Methods; Autoclave Engineers, Erie, Pa.).

Prior to contacting the biomass with an aqueous solution comprising ammonia, vacuum may be applied to the vessel containing the biomass. By evacuating air from the pores of the biomass, better penetration of the ammonia into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The contacting of the biomass with an aqueous solution comprising ammonia is carried out at a temperature of from about 4° C. to about 200° C. Initial contact of the biomass with ammonia at 4° C., allowing impregnation at this temperature, was found to increase the efficiency of saccharification over non-pretreated native biomass. In another embodiment, said contacting of the biomass is carried out at a temperature of from about 75° C. to about 150° C. In still another embodiment, said contacting of the biomass is carried out at a temperature of from greater than 90° C. to about 150° C.

The contacting of the biomass with an aqueous solution comprising ammonia is carried out for a period of time up to about 25 hrs. Longer periods of pretreatment are possible, however a shorter period of time may be preferable for practical, economic reasons. Typically a period of ammonia contact treatment is about 8 hours or less. Longer periods may provide the benefit of reducing the need for application of energy for breaking-up the biomass, therefore, a period of time up to about 25 hrs. may be preferable.

In one embodiment, the pretreatment process may be performed at a relatively high temperature for a relatively short period of time, for example at from about 100° C. to about 150° C. for about 5 min to about 2 hr. In another embodiment, the pretreatment process may be performed at a lower temperature for a relatively long period of time, for example from about 75° C. to about 100° C. for about 2 hr to about 8 hr. In still another embodiment, the pretreatment process may be performed at room temperature (approximately 22-26° C.) for an even longer period of time of about 24 hr. Other temperature and time combinations intermediate to these may also be used.

For the pretreatment process, the temperature, time for pretreatment, ammonia concentration, concentration of one or more additional bases, biomass concentration, biomass type and biomass particle size are related; thus these variables may be adjusted as necessary to obtain an optimal product to be contacted with a saccharification enzyme consortium.

A plasticizer, softening agent, or combination thereof, such as polyols (e.g., glycerol, ethylene glycol), esters of polyols (e.g., glycerol monoacetate), glycol ethers (e.g., diethylene glycol), acetamide, ethanol, and ethanolamines, may be added in the pretreatment process (i.e., step (a)). A plasticizer may be added as a component of the aqueous ammonia solution, as a separate solution, or as a dry component.

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-aqueous ammonia mixture. Reactor design is discussed in Lin, K.-H., and Van Ness, H. C. (in Perry, R.H. and Chilton, C. H. (eds), Chemical Engineer's Handbook, 5$^{th}$ Edition (1973) Chapter 4, McGraw-Hill, N.Y.). The pretreatment reaction may be carried out as a batch process, or as a continuous process.

It is well known to those skilled in the art that a nitrogen source is required for growth of microorganisms during fermentation; thus the use of ammonia during pretreatment provides a nitrogen source and reduces or eliminates the need to supplement the growth medium used during fermentation with a nitrogen source. If the pH of the pretreatment product exceeds that at which saccharification enzymes are active, or exceeds the range suitable for microbial growth in fermentation, acids may be utilized to reduce pH. The amount of acid used to achieve the desired pH may result in the formation of salts at concentrations that are inhibitory to saccharification enzymes or to microbial growth. In order to reduce the amount of acid required to achieve the desired pH and to reduce the raw material cost of $NH_3$ in the present pretreatment process, ammonia gas may be evacuated from the pretreatment reactor and recycled. Typically, at least a portion of the ammonia is removed, which reduces the pH but leaves some nitrogen that provides this nutrient for use in subsequent fermentation.

In order to obtain sufficient quantities of sugars from biomass, the biomass may be pretreated with an aqueous ammonia solution one time or more than one time. Likewise, a saccharification reaction can be performed one or more times. Both pretreatment and saccharification processes may be repeated if desired to obtain higher yields of sugars. To assess performance of the pretreatment and saccharification processes, separately or together, the theoretical yield of sugars derivable from the starting biomass can be determined and compared to measured yields.

Saccharification:

Following pretreatment, the product comprises a mixture of ammonia, partially degraded biomass and fermentable sugars. Prior to further processing, ammonia may be removed from the pretreated biomass by applying a vacuum. Removing ammonia lowers the pH, and thus less neutralizing acid is used to obtain the desired pH for saccharification and fermentation. This results in a lower salt load in the pretreatment mixture. Typically some ammonia remains, which is desired to provide a nitrogen source for fermentation.

The pretreatment mixture is then further hydrolyzed in the presence of a saccharification enzyme consortium to release oligosaccharides and/or monosaccharides in a hydrolyzate. Saccharification enzymes and methods for biomass treatment are reviewed in Lynd, L. R., et al. (Microbiol. Mol. Biol. Rev. (2002) 66:506-577). In one preferred embodiment, the entire pretreatment mixture comprising both soluble and insoluble fractions is utilized in the saccharification reaction.

In another embodiment, prior to saccharification, the aqueous fraction comprising ammonia and solubilized sugars may be separated from insoluble particulates remaining in the mixture. Methods for separating the soluble from the insoluble fractions include, but are not limited to, decantation and filtration. The insoluble particulates may be recycled to the pretreatment reactor. The insoluble particulates may optionally be washed with an aqueous solvent (e.g., water) to remove adsorbed sugars prior to being recycled to the pretreatment reactor. The insoluble fraction may then be subjected to additional treatment with aqueous ammonia solution as described above for pretreatment, followed by saccharification with a saccharification enzyme consortium. The soluble fraction may also be concentrated-prior to saccharification using a suitable process, such as evaporation.

Prior to saccharification, the pretreatment product may be treated to alter the pH, composition or temperature such that the enzymes of the saccharification enzyme consortium will be active, thus providing suitable conditions to produce fermentable sugars. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed, such as by bubbling, into the pretreatment product while monitoring the pH, until the desired pH is achieved. The temperature may be brought to a temperature that is compatible with saccharification enzyme activity, as noted below. Any cofactors required for activity of enzymes used in saccharification may be added.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. The pH optimum can range from about 2 to about 11. In another embodiment, the pH optimum used with the saccharification enzyme consortium in the present method ranges from about 4 to about 10.

The saccharification can be performed for a time of about several minutes to about 120 hr, and preferably from about several minutes to about 48 hr. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentable sugars released from biomass can be used by suitable microorganisms to produce target chemicals. Following saccharification, but prior to fermentation, the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the microorganism(s) used during fermentation and the pH used during saccharification, the pH may be adjusted to that suitable for fermentation. In addition, the saccharification mixture may be supplemented with additional nutrients required for microbial growth. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration. The saccharification mixture may be used as a component of a fermentation broth, for example, making up between about 100% and about 10% of the final medium. Suitable fermentation conditions are achieved by adjusting these types of factors for the growth and target chemical production by a biocatalyst.

Temperature and/or headspace gas may also be adjusted, depending on conditions useful for the fermentation microorganism(s). Fermentation may be aerobic or anaerobic. Fermentation may occur subsequent to saccharification, or may occur concurrently with saccharification by simultaneous saccharification and fermentation (SSF). SSF can keep the sugar levels produced by saccharification low, thereby reducing potential product inhibition of the saccharification enzymes, reducing sugar availability for contaminating microorganisms, and improving the conversion of pretreated biomass to monosaccharides and/or oligosaccharides.

Target chemicals that may be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include *Escherichia, Zymomonas, Saccharomyces, Candida, Pichia, Streptomyces, Bacillus, Lactobacillus*, and *Clostridium*. In another embodiment, biocatalysts may be selected from the group consisting of recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*.

Many biocatalysts used in fermentation to produce target chemicals have been described and others may be discovered, produced through mutation, or engineered through recombinant means. Any biocatalyst that uses fermentable sugars produced in the present method may be used to make the target chemical(s) that it is known to produce, by fermentation in the present method.

Fermentation of carbohydrates to acetone, butanol, and ethanol (ABE fermentation) by solventogenic *Clostridia* is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Genetically modified strains of *E. coli* have also been used as biocatalysts for ethanol production (Underwood et al., (2002) Appl. Environ. Microbiol.68:6263-6272). A genetically modified strain of *Zymomonas mobilis* that has improved production of ethanol is described in US 2003/0162271 A1.

Lactic acid has been produced in fermentations by recombinant strains of *E. coli* (Zhou et al., (2003) Appl. Environ. Microbiol. 69:399-407), natural strains of *Bacillus* (US20050250192), and Rhizopus oryzae (Tay and Yang (2002) Biotechnol. Bioeng. 80:1-12). Recombinant strains of *E. coli* have been used as biocatalysts in fermentation to produce 1,3 propanediol (U.S. Pat. Nos. 6,013,494, 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17crl (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:113643). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-Ul-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium, Brevibacterium,* and *Serratia*. For example, production of histidine using a strain resistant to a histidine analog is described in Japanese Patent Publication No. 8596/81 and using a recombinant strain is described in EP 136359. Production of tryptophan using a strain resistant to a tryptophan analog is described in Japanese Patent Publication Nos. 4505/72 and 1937/76. Production of isoleucine using a strain resistant to an isoleucine analog is described in Japanese Patent Publication Nos. 38995/72, 6237/76, 32070/79. Production of phenylalanine using a strain resistant to a phenylalanine analog is described in Japanese Patent Publication No. 10035/81. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 37235/79 and 150381/82) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant. strain of *Corynebacterium lilium* (Kumar et al, (2005) Bioresour. Technol. 96: 287-294).

Useful peptides, enzymes, and other proteins have also been made by biocatalysts (for example, in U.S. Pat. No. 6,861,237, U.S. Pat. No. 6,777,207, U.S. Pat. No. 6,228,630).

The pretreatment and saccharification of biomass to fermentable sugars, followed by fermentation of the sugars to a target chemical is exemplified in Example 9 herein for the production of ethanol from pretreated corn cobs using *Z. mobilis* as the biocatalyst for the fermentation of sugars to ethanol. The present method may also be used for the production of 1,3-propanediol from biomass. Biomass undergoes pretreatment and saccharification according to the present method; following (or during) saccharification, *E. coli* is used to produce 1,3-propanediol as described in Example 10 herein.

Target chemicals produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

EXAMPLES

General Methods and Materials

The Following Abbreviations are Used:

"HPLC" is High Performance Liquid Chromatography, "C" is Centigrade, "kPa" is kilopascal, "m" is meter, "mm" is millimeter, "kW" is kilowatt, "μm" is micrometer, "μL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass.

Sulfuric acid, ammonium hydroxide, acetic acid, acetamide, yeast extract, 2-morpholinoethanesulfonic acid (MES), potassium phosphate, glucose, xylose, tryptone, sodium chloride and citric acid were obtained from Sigma-Aldrich (St. Louis, Mo.).

Pretreatment Reactors

Zipperclave® Reactor

The 4-liter Zipperclave® reactor (Autoclave Engineers, Erie, Pa.) is a batch pressure vessel equipped with a 2.5-liter Hastelloy® pail for the biomass charge and an agitator to mix the biomass. The reactor vessel is encircled by an electrical heater controlled at the desired pretreatment temperature. Direct steam injection is also used to rapidly bring the biomass up to pretreatment temperature. Steam pressure is adjusted and controlled to maintain the desired pretreatment temperature. Steam condensate formed by heating the Zipperclave® reactor head plate, vessel and outside of the pail drain to a reservoir formed between the pail and the inner wall of the reactor to prevent excessive dilution of the pretreated slurry.

Jaygo Reactor

The Jaygo reactor is a 130-liter (approximately 51 cm diameter×91 cm length), horizontal paddle type reactor (Jaygo Manufacturing, Inc., Mahwah, N.J.) fabricated of Hastelloy® C-22 alloy. The reactor is equipped with a steam jacket capable of heating to approximately 177° C. (862 kPa). Direct steam injection is also used to rapidly bring the biomass up to pretreatment temperature. Steam pressure is adjusted and controlled to maintain the desired pretreatment temperature. Numerous ports allow injection of other solvents and hot liquids.

Steam Gun Reactor Batch Digestion System

The 4-liter steam gun reactor (Autoclave Engineers, Erie, Pa.) is a steam-jacketed reactor consisting of a length of 102 mm schedule 80 Hastelloy® pipe closed by two ball valves. Additional electrical heaters are placed on all exposed, non-jacketed surfaces of the reactor and controlled to the pretreatment set point temperature. Direct steam injection is also used to rapidly bring the biomass up to pretreatment temperature. Steam pressure is adjusted and controlled to maintain the desired pretreatment temperature. The bottom of the reactor is necked down to 51 mm. All pretreated material exits through a replaceable die at the bottom of the reactor and is collected in a nylon (Hotfill®) 0.21 $m^3$ bag supported within a heavy walled, jacketed, and cooled flash tank.

Disc Refiner

The disc refiner is a Sprout Waldron model 30.5 cm refiner (Andritz, Inc., Muncy, Pa.) equipped with a 11 kW electric motor. The gap between the stationary and rotating plates is variable. The feed auger speed is also variable, from 0-88 rpm. The inlet to the refiner was modified with six injection ports to allow the introduction of steam, hot water, or other sweep gases and liquids just ahead of the rotating refiner plate. The refiner was equipped with plates (Durametal, Corp., Tulatin, Oreg.) in either pattern D2A506 in Ni-Hard or pattern 18034-A in Ni-Hard.

Pretreatment and Enzymatic Hydrolysis Reactor (PEHR)

The 9L PEHReactor (constructed at NREL, Golden, Colo.; see co-pending U.S. patent application CL3447) has an approximately 15 cm×51 cm stainless steel reaction vessel with an injection lance for introduction of processing reactants. The injection lance is connected using a rotary joint to a port in a cover on one end of the vessel, which has an additional port for vessel access. Four baffles run the length of the vessel wall, and are attached perpendicularly to the wall. The baffles and twenty-two ceramic attrition media cylinders of 3.2 cm×3.2 cm (E.R. Advanced Ceramics, East Palestine, Ohio), free floating in the vessel, apply mechanical mixing of biomass and reactant as the vessel is rotated, promoting assimilation of reactant into the biomass. The PEHReactor is placed on a Bellco Cell-Production Roller Apparatus (Bellco Technology, Vineland, N.J.) which provides a mechanism for rotation, and the reactor with roller apparatus is housed in a temperature controlled chamber which provides heat. Vacuum and pressure may be applied to the reaction vessel by attaching external sources to the lance-connected port in the cover.

Analytical Methods

Cellulose Quantitation

The amount of cellulose in each starting biomass sample was determined using methods well known in the art, such as ASTM E1758-01 "Standard method for the determination of carbohydrates by HPLC".

Measurement of Sugar, Acetamide, Lactic Acid and Acetic Acid Content

Soluble sugars (glucose, cellobiose, xylose, galactose, arabinose and mannose), acetamide, lactic acid and acetic acid in saccharification liquor were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with appropriate guard columns. The sample pH was measured and adjusted to 5-6 with sulfuric acid if necessary. The sample was then passed through a 0.2 μm syringe filter directly into an HPLC vial. The HPLC run conditions were as follows:

Biorad Aminex HPX-87P (for carbohydrates):
  Injection volume: 10-50 μL, dependent on concentration and detector limits
  Mobile phase: HPLC grade water, 0.2 μm filtered and degassed
  Flow rate: 0.6 mL/minute
  Column temperature: 80-85° C., guard column temperature <60° C.
  Detector temperature: as close to main column temperature as possible
  Detector: refractive index
  Run time: 35 minute data collection plus 15 minute post run (with possible adjustment for later eluting compounds)

Biorad Aminex HPX-87H (for carbohydrates, acetamide, lactic acid, acetic acid, and ethanol)
  Injection volume: 5-10 μL, dependent on concentration and detector limits
  Mobile phase: 0.1 N Sulfuric acid, 0.2 μm filtered and degassed
  Flow rate: 0.6 mL/minute
  Column temperature: 55° C.
  Detector temperature: as close to column temperature as possible
  Detector: refractive index
  Run time: 25-75 minute data collection After the run, concentrations in the sample were determined from standard curves for each of the compounds.

Example 1

Stover Pretreatment at High Biomass Concentration, High Temperature and Comparison of Ammonia Concentrations The Zipperclave® reactor vessel and head plate were pre-heated to the target pretreatment temperature before introduction of the biomass charge by cycling steam into the reactor and venting several times. Condensate formed during pre-heating was removed by vacuum aspiration before pretreatment. The Hastelloy® pail was loaded with 0.635-cm (¼-in.) milled stover (100 g, dry weight basis) and inserted into the pre-warmed reactor. The reactor agitator was set to 20 rpm while a vacuum (approximately 85 kPa) was applied to the vessel interior and biomass charge. Ammonium hydroxide solution of the necessary strength to give a dry weight of biomass concentration of 30 weight percent relative to the weight of the biomass-aqueous ammonia mixture, as well as the desired ammonia concentration listed in Table 1, was injected near the bottom of the vessel with a spray type nozzle. Test samples had a final ammonia concentration of 12% relative to dry weight of biomass, while samples with a final ammonia concentration of 35% relative to dry weight of biomass were used as a comparison. When the temperature of the biomass charge reached 50° C., steam was introduced near the bottom of the reactor to fluidize and raise the temperature of the biomass charge to either 140° C. or 170° C. At the end of pretreatment, the reactor was depressurized through a vent condenser, and a vacuum (approximately 85 kPa) was applied for 3 minutes to lower the temperature and remove additional ammonia from the pretreated slurry prior to opening the reactor and recovering the pretreated biomass.

Whole, unwashed pretreatment slurry containing 0.5 g of cellulose (based on initial feedstock composition) was added in a final volume of 50 mL to a 125-mL shake flask. Acetic acid (10-100 μL) was added, to titrate the pH of the ammonia-pretreated biomass to 5.0 before enzyme addition because of the sensitivity of the enzymes to high pH environments. The pH was controlled at 5.0 during saccharification by the addition of 50 mM citrate buffer, and the temperature was maintained at 50° C. Spezyme® CP cellase (Genencor International, Rochester, N.Y.) was added to the concentration listed for each sample in Table 1. The sugar content of the resulting saccharification liquor was determined after 96 hr saccharification according to the sugar measurement protocol described in the General Methods. Sugar release after 96 hr is shown in Table 2. Controls for this experiment were 1) untreated corn stover, which yielded 23% of the theoretical yield of glucose (using 56 mg cellulase /g cellulose) and 2) steam (140° C.) pretreated corn stover, which yielded 40% of the theoretical yield of glucose (using 56 mg cellulase /g cellulose); xylose was not measured for the controls.

TABLE 1

Sugar release from pretreated corn stover with 96 hr saccharification

| Ammonia (g/100 g DWB) | Pretreat Temp (° C.) | Pretreat Time | Cellulase (mg/g cellulose) | Glucose Release (% theoret) | Xylose Release (% theoret) |
|---|---|---|---|---|---|
| 35 | 170 | 5 min | 56 | 68.0 | 60.0 |
| 12 | 170 | 5 min | 56 | 58.5 | 45.3 |
| 12 | 170 | 5 min | 11 | 40.8 | 27.1 |
| 35 | 140 | 5 min | 56 | 54.5 | 41.5 |
| 12 | 140 | 5 min | 56 | 53.0 | 31.4 |
| 12 | 140 | 5 min | 11 | 38.9 | 17.1 |
| 12 | 140 | 15 min | 56 | 62.4 | 49.6 |
| 12 | 140 | 15 min | 11 | 41.7 | 33.6 |

DWB: dry weight of biomass.

These results indicate that a pretreatment using ammonia at 12% for 15 minutes at 140° C., followed by saccharification, releases more glucose and xylose than when pretreatment is using 35% ammonia for 5 minutes at 140° C. Thus, advantages of using lower ammonia can be incorporated by a small increase in pretreatment time.

Example 2

Stover Pretreatment at High Biomass Concentration, Low Temperature, and Very Low Ammonia The Jaygo reactor was charged with 0.635-cm milled stover (13 kg, dry weight basis). A vacuum (67.7 kPa) was applied to the vessel, and dilute ammonium hydroxide solution was injected to give an ammonia concentration of 6.2 g ammonia/100 g dry weight of biomass and a dry weight of biomass concentration 30 weight percent relative to total weight of the biomass-aqueous ammonia mixture. The vacuum was relieved, and steam was applied to the jacket to heat the stover to 100° C. The soaked stover was held at temperature for 8 hr with constant mixing at 32 rpm, then allowed to cool overnight with continued mixing of the resulting slurry.

Whole, unwashed pretreatment slurry containing 0.5 g of cellulose (based on initial feedstock composition) was added in a final volume of 50 mL to a 125-mL shake flask. Acetic acid (10-100 μL) was added, if necessary, to titrate the pH of the ammonia-pretreated biomass to 5.0 before enzyme addition because of the sensitivity of the enzymes to high pH environments. The pH was controlled at 5.0 during saccharification by the addition of 50 mM citrate buffer, and the temperature was maintained at 50° C. Spezyme® CP cellulase (Genencor International, Rochester, N.Y.) was added to 56 mg/g cellulose. The sugar content of the resulting saccharification liquor was determined after 96 hr saccharification according to the sugar measurement protocol described in the General Methods and is shown in Table 2.

TABLE 2

Sugar release from pretreated corn stover at 96 hr

| Ammonia (g/100 g DWB) | Pretreat Temp (° C.) | Pretreat Time | Cellulase (mg/g cellulose) | Glucose Release (% theoret) | Xylose Release (% theoret) |
|---|---|---|---|---|---|
| 6.2 | 100 | 8 hr | 56 | 63.9 | 44.8 |

The results indicate that these very low ammonia concentrations and low temperature pretreatment conditions, (for a period of 8 hr) are as effective as using 12% ammonia at 140° C. for 15 min.

Example 3

Cob Pretreatment at High Biomass Concentration, Low Temperature, and Very Low Ammonia Concentration Followed by High Biomass Concentration Saccharification Whole or fractured corn cobs (approximately 13 kg, dry weight basis) were loaded into the Jaygo reactor. Cobs were fractured by passing through the disk refiner (General Methods) equipped with plates C-2975. Resulting fractured cobs were passed through a 1.27 cm screen. Any pieces retained were passed through the disk refiner again with a 0.5 cm smaller gap. A vacuum was applied to the reactor, and dilute ammonium hydroxide solution was injected to give the final desired ammonia concentration (2% or 6%) and concentration of dry biomass (30% or 40%), as given in Table 3. The vacuum was relieved and steam was applied to the jacket to heat the cobs while soaking to a temperature of 93° C. for the whole cob sample and 85° C. for fractured cob samples. Short periods of increased agitator speeds (up to 96 rpm) were applied in an effort to increase the heating rate. The soaked cobs were held at temperature for 4 or 8 hr with constant mixing at 32 rpm then allowed to cool overnight with continued mixing.

Before pretreated biomass was removed from the reactor, the reactor was put under vacuum at 90° C. to strip ammonia out of the pretreated biomass. Before saccharification, the pH of the pretreated cob biomass was adjusted to 5.5 with solid citric acid. About 10 kg of pretreated whole cob was saccharified in the Jaygo reactor at 50° C. About 1400 g of pretreated fractured cob was added to the PEHReactor, along with 22 ceramic attrition cylinders (3.2 cm diameter×3.2 cm long; E. R. Advanced Ceramics, East Palestine, Ohio), for saccharification. An enzyme mixture of 28 mg Spezyme CP®/g cellulose in untreated stover plus 28 mg/g cellulose Multifect Xylanase® was used for each saccharification reaction. The final dry weight of biomass concentration at the beginning of each saccharification was 30% relative to the total weight of the pretreated biomass-saccharification enzyme consortium mixture. The PEHReactor was rotated axially at 19 rpm while maintaining a temperature of 50° C. The sugar content of the resulting saccharification liquor was determined according to the sugar measurement protocol in the General Methods. Sugar release after 96 hr is shown in Table 3.

temperature of the reactor contents was between 27° C. to 31° C. The pH of the soaked/pretreated biomass was approximately 7.5.

Pretreated biomass was removed from the Jaygo reactor and transferred to the PEHReactor for saccharification at a final dry weight of biomass concentration at the beginning for saccharification of 30% relative to the total weight of the

TABLE 3

Sugar release from pretreated corn cobs using a high concentration of biomass (by dry weight) during saccharification.

| Feedstock | Pretreat time (hr) | Pretreatment temp. (° C.) | Ammonia (g/100 g DWB) | DWB (Pretreat) | DWB (Saccharif.) | Glucose Release (% theoret) | Xylose Release (% theoret) |
|---|---|---|---|---|---|---|---|
| Whole cob | 8 hr | 93 | 6 | 40% | 30% | 54.4 | 46.1 |
| Fractured cob | 4 hr | 85 | 2 | 30% | 30% | 42.1 | 19.1 |

DWB: dry weight of biomass (percent is calculated relative to the total weight of the mixture)

Example 4

Cob Pretreatment at High Biomass Concentration, High Temperature, and Very Low Ammonia Concentration Followed by High Biomass Concentration Saccharification Fractured corn cobs (13 kg, dry basis) were loaded into the Jaygo reactor. After pulling a vacuum on the reactor, ammonium hydroxide solution of the proper strength to give 2% ammonia and 30% dry weight of biomass concentration was pumped into the reactor with 32 rpm mixing at room temperature. The contents of the reactor were then heated to 95° C. using low-pressure jacket steam. Once the reactor reached 95° C., direct steam injection was used to heat the contents of the reactor to 145° C. When the reactor reached 145° C., the reactor contents were held at that temperature for 20 minutes using jacket steam and some direct steam injection. After 20 minutes, a vacuum was pulled on the vent to the reactor and the shredder motor was turned on for 5 minutes. After 1 hr the cooling water to the jacket was turned on. The contents of the Jaygo reactor were cooled to between 33° C. and 37° C.; then $CO_2$ was used to pressurize the reactor to 138 kPa. The pressurized $CO_2$ atmosphere was maintained for 30 min. The final pretreated biomass-saccharification enzyme consortium mixture. The pH was then adjusted to 5.5 with solid citric acid, and the material digested with 28 mg Spezyme CP®/g cellulose and 28 mg Multifect Xylanase®/g cellulose in untreated cob as described in Example 3. The sugar content of the resulting saccharification liquor was determined according to the sugar measurement protocol in the General Methods. The sugar release after 96 hr digestion is shown in Table 4.

TABLE 4

Sugar release from pretreated corn cobs using a high concentration of biomass (by dry weight) during saccharification.

| Feedstock | Pretreat time (hr) | Pretreatment temperature (° C.) | Ammonia (g/100 g DWB) | DWB (Pretreat) | DWB (Saccharif.) | Glucose Release (% theoret) | Xylose Release (% theoret) |
|---|---|---|---|---|---|---|---|
| Fractured cob | 20 min | 145 | 2 | 30% | 30% | 35.9 | 45.4 |

Example 5

Pretreatment with Addition of Plasticizer

Whole cob was pretreated as described in Example 3 at a dry weight of biomass concentration of about 30% relative to the total weight of the biomass-aqueous ammonia mixture, 2 weight percent ammonia relative to dry weight of biomass, 100° C., for 8 hr in the Jaygo reactor with 3 weight percent relative to dry weight of biomass of glycerol added to act as a plasticizer. After pretreatment, the pH of the resulting material was adjusted to 5 with solid citric acid. Pretreated cob was then digested as described in Example 3. An enzyme mixture of 28 mg Spezyme CP®/g cellulose in untreated stover plus 28 mg/g cellulose Multifect Xylanase® in untreated cob was used. After 96 hr digestion, glucose concentration was 92.3 g/L and xylose concentration was 54.4 g/L.

Example 6

Disc Refining of Pretreated Biomass

Stover was pretreated in the manner described in Example 1, with different samples having low ammonia (12%) or comparative ammonia (35%) concentrations, and temperature, time, and enzyme conditions as listed in Table 5. Whole cob was pretreated as described in Example 3 with different samples having very low ammonia (3% or 6%), and other conditions as listed in Table 5. Following pretreatment, the samples were passed through a Sprout Waldron disc refiner. The gap between the stationary plate and rotating plate was set at 0.254 mm (0.010 inch) and the feed auger speed at 7 rpm. Refined material was saccharified as described in Example 2 and the sugar content of the resulting saccharification liquor was determined according to the sugar measurement protocol in the General Methods. Results of the saccharification at 96 hr are shown in Table 5. The results showed that with disc refining prior to saccharification, better digestibility was attained, or use of lower enzyme concentrations was effective.

TABLE 5

Digestibility of pretreated material that was disc refined prior to saccharification

| Feedstock | Pretreat time | Pretreat Temp (° C.) | Ammonia (g/100 g DWB) | Cellulase (mg/g cellulose) | Xylanase Added (mg/g cellulose) | Glucose Release (% theoret) | Xylose Release (% theoret) |
|---|---|---|---|---|---|---|---|
| Stover | 5 min | 170 | 35 | 56 | 0 | 87.3 | 72.5 |
| Stover | 5 min | 140 | 35 | 56 | 0 | 76.9 | 59.4 |
| Stover | 5 min | 170 | 12 | 56 | 0 | 58.8 | 39.9 |
| Stover | 5 min | 170 | 12 | 28 | 28 | 68.4 | 62.3 |
| Stover | 5 min | 140 | 12 | 56 | 0 | 69.1 | 48.6 |
| Stover | 5 min | 140 | 12 | 11 | 0 | 52.6 | 31.5 |
| Stover | 15 min | 140 | 12 | 56 | 0 | 61.8 | 40.1 |
| Stover | 15 min | 140 | 12 | 28 | 28 | 66.7 | 54.1 |
| Stover | 8 hr | 100 | 6 | 56 | 0 | 79.9 | 59.6 |
| Cob | 8 hr | 93 | 6 | 56 | 0 | 82.4 | 51.7 |
| Cob | 8 hr | 93 | 6 | 28 | 28 | 83.1 | 58.6 |
| Cob | 8 hr | 100 | 2 | 56 | 0 | 68.0 | 38.5 |
| Cob | 8 hr | 100 | 2 | 28 | 28 | 81.0 | 57.3 |

Example 7

Steam Gun Treatment of Pretreated Biomass

Stover was pretreated as described in Example 1 using conditions of 30% dry weight of biomass relative to total weight of biomass-aqueous ammonia mixture, 6 weight percent ammonia relative to DWB, 100° C., 8 hr, in the Jaygo reactor. Cob was pretreated as described in Example 3 using conditions of 40% dry weight of biomass relative to total weight of biomass-aqueous ammonia mixture, 6 weight percent ammonia relative to DWB, 93° C., 8 hr, in the Jaygo reactor. Samples of each pretreated biomass were separately loaded into a 4-liter steam gun reactor. Pretreated material was subjected to 170° C. for 5 min, or 140° C. for 20 min before being released through a die. The resulting material was saccharified as described in Example 2. Results are given in Table 6 below. The results showed that steam gun treatment prior to saccharification improved release of glucose.

TABLE 6

Digestibility of pretreated material after steam gun treatment

| Feedstock | Steam Gun Temp (° C.) | Steam Gun Time (min) | Cellulase (mg/g cellulose) | Xylanase Added (mg/g cellulose) | Glucose Release (% theoret) | Xylose Release (% theoret) |
|---|---|---|---|---|---|---|
| Stover | 170 | 5 | 56 | 0 | 77.5 | 37.5 |
| Stover | 170 | 5 | 28 | 28 | 82.5 | 64.4 |
| Stover | 140 | 20 | 56 | 0 | 73.4 | 43.4 |
| Stover | 140 | 20 | 28 | 28 | 82.2 | 66.9 |
| Cob | 170 | 5 | 28 | 28 | 70.7 | 47.4 |
| Cob | 170 | 5 | 11 | 11 | 49.1 | 38.9 |
| Cob | 140 | 20 | 28 | 28 | 55.7 | 39.0 |
| Cob | 140 | 20 | 11 | 11 | 32.9 | 24.0 |

Example 8

Modeling of Pretreatment with Ammonia Recycle

Advantages of ammonia recycle were examined with Aspen models (Aspen Technologies, Cambridge, Mass., version 12.1) for two pretreatment schemes: low temperature (85° C.), long residence time (4 hr) and high temperature (130° C.), short residence time (20 min). In each model there was a series of three flash tanks operating at successively lower pressures after the pretreatment reactor to provide a means for ammonia recycle. As the feed stream entered into each tank, it split into vapor and liquid fractions due to the reduction in pressure. The vapor fraction was recycled to pretreatment, while the liquid fraction went on to the next step in the process. Assuming 2 weight percent ammonia relative to DWB and approximately 27% dry weight of biomass relative to the total weight of the biomass-aqueous ammonia mixture in pretreatment, ammonia supplied fresh and from the recycle streams for each process are shown in Table 7. In both models, the flash tanks operated in similar fashion so that ammonia recycle was similar. For both scenarios, more than half of the required ammonia was supplied through recycle, reducing the need for and cost of fresh ammonia.

TABLE 7

Ammonia recycle in pretreatment - Aspen model results.

| | High T/short residence time | | Low T/long residence time | |
|---|---|---|---|---|
| | Ammonia flow rate into pretreatment (kg/hr) | Fraction total ammonia in pretreatment | Ammonia flow rate into pretreatment (kg/hr) | Fraction total ammonia in pretreatment |
| Fresh NH$_3$ | 518.6 | 43.5% | 520.2 | 43.7% |
| From 1$^{st}$ flash | 371.2 | 31.2% | 374.4 | 31.4% |
| From 2$^{nd}$ flash | 137.2 | 11.5% | 135.4 | 11.4% |
| From 3$^{rd}$ flash | 164.1 | 13.8% | 161.2 | 13.5% |
| Total | 1191.2 | 100% | 1191.2 | 100% |

Example 9

Ethanol Production from Low Ammonia-Pretreated and Saccharified Cob Biomass, and Comparison to High Ammonia-Pretreated and Saccharified Stover Cob hydrolyzate was generated by pretreating whole cobs in the Jaygo reactor for 8 hr at 93° C. with 6 weight percent ammonia relative to dry weight of biomass at a dry weight of biomass concentration of 40 weight percent relative to the total weight of the biomass-aqueous ammonia mixture, as described in Example 3. After pretreatment, ammonia was removed by heating the reactor to 90° C. under vacuum. The pH of the pretreated biomass was then adjusted to 5 with sulfuric acid. The pretreated biomass was saccharified in the Jaygo reactor at 30% dry weight of biomass relative to the total weight of the pretreated biomass-saccharification enzyme consortium mixture with 28 mg/g cellulose Spezyme® cellulase and 28 mg/g cellulose Multifect® xylanase for 168 hr at 50° C. and pH 5. The resulting hydrolyzate was used for fermentation of *Zymomonas mobilis* 8b in Sixfors fermentors (INFORS AG, Switzerland). *Zymomonas mobilis* 8b is a strain of *Zymomonas mobilis* that has been genetically engineered to give improved, over wild type, production of ethanol and is described in US Patent Application Publication 2003/0162271 A1 (Examples IV, VI and XII). The cob hydrolyzate comprised 78 g/L glucose, 51 g/L xylose, 6 g/L acetamide, and 7 g/L acetic acid. The cob hydrolyzate was used at 40% and 80% strength, with the balance of the medium being concentrated aqueous medium consisting of yeast extract, and KH$_2$PO$_4$ in quantities such that their concentrations in the final slurry were about 5 g/L, and 2 g/L respectively. Additionally, in the 40% hydrolyzate slurry, glucose and xylose were added in quantities sufficient to bring their concentrations to their same levels as in the 80% hydrolyzate slurry. The fermentation was carried out at 37° C. Agitation in the fermentors was 100 rpm, and pH was maintained at 5.5 by addition of 2 N KOH. The results are shown in Table 8. Sugars and ethanol were analyzed as described in General Methods.

For comparison, stover hydrolyzate was generated by pretreating stover with 35 weight percent ammonia relative to dry weight of biomass at a dry weight of biomass concentration of about 30 weight percent relative to the total weight of the biomass-aqueous ammonia mixture at 170° C. for 5 min in the Zipperclave® reactor, as described in Example 1. The pretreated biomass was enzymatically digested at 30% dry weight of biomass relative to the total weight of the pretreated biomass-saccharification enzyme consortium mixture with 224 mg/g cellulose Spezyme CP® cellulase at 50° C. and pH 5 to generate a high sugar concentration hydrolyzate for fermentation testing. The resulting hydrolyzate comprised 88 g/L glucose, 52 g/L xylose, 9 g/L acetic acid and 15 g/L lactic acid. For ethanol production, *Zymomonas mobilis* 8b was fermented on either 40% or 80% (v/v) hydrolyzate slurry. The remaining volume was made up of concentrated aqueous medium consisting of yeast extract, KH$_2$PO$_4$ and MES buffer in quantities such that their concentrations in the final slurry would be about 10 g/L, 2 g/L and 0.1 M, respectively. Additionally, in the 40% hydrolyzate slurry, glucose and xylose were added in quantities sufficient to bring their concentrations to the same levels as in the 80% hydrolyzate slurry. Fermentation was done at 30° C. and pH 6 in 25 ml shake flasks with 20 ml working volume. Agitation was maintained at 150 rpm. Analysis was as for the cob hydrolyzate fermentation sample and results are given in Table 8.

TABLE 8

Sugar utilization and ethanol yields in fermentation on cob and stover hydrolyzates.

| | Stover (120 hr endpoint) | | Cob (72 hr endpoint) | |
|---|---|---|---|---|
| | 40% Hydrolyzate | 80% Hydrolyzate | 40% Hydrolyzate | 80% Hydrolyzate |
| Glucose Utilized | 100% | 97% | 99% | 97% |
| Xylose Utilized | 90% | 16% | 96% | 57% |
| Ethanol Yield | 77% | 53% | 98% | 87% |

These results showed that fermentation to produce ethanol from cob hydrolyzate pretreated with low ammonia was more efficient than from stover pretreated with high ammonia.

Example 10

1-3 Propanediol Production from Very Low Ammonia-Pretreated and Saccharified Cob Biomass Hydrolyzate generated from pretreatment and saccharification of cob was fermented to produce 1,3-propanediol. Hydrolyzate was generated by pretreating cob pieces in the steam gun reactor. First cob biomass was loaded in the PEHReactor (described in General Methods), a vacuum applied, and dilute ammonium hydroxide solution was injected to give an ammonia concentration of 4 g ammonia/100 g dry weight biomass and a dry weight of biomass concentration of 30 g dry weight of biomass/100 g total biomass-aqueous ammonia mixture. The reactor vessel charged with ammonia and cob was rotated at 4° C. for 30 min. The contents were transferred to the steam gun reactor (described in General Methods), the temperature increased to 145° C., and the mixture was held at temperature for 20 minutes. Material from the steam gun was discharged into a flash tank, and vacuum was maintained on the flash tank to aid ammonia removal. After pH adjustment, the pretreated biomass was saccharified at 30 g dry weight of biomass/100 g pretreated biomass-saccharification enzyme consortium mixture with 28.4 mg/g cellulose Spezyme CP® cellulase and 10.1 mg active protein/g cellulose enzyme consortium consisting of β-glucosidase, xylanase, β-xylosidase and arabinofuranosidase for 72 hr at 50° C. and pH 5.5. The resulting hydrolyzate was used as a source of fermentable sugar for conversion to 1,3-propanediol by recombinant *E. coli* strain RJ8n pBE93-k1. The construction of strain RJ8n pBE93-k1 is described in detail in PCT application WO/2004/018645 (Example 7), and it is a derivative of strain RJ8n, described in U.S. Pat. No. 6,358,716. The hydrolyzate was used at 10% with the balance being aqueous medium consisting of 7.5 g/L $KH_2PO_4$, 2.0 g/L citric acid*$H_2O$, 4.0 ml/L 28% $NH_4OH$, 3.0 g/L$(NH_4)_2SO_4$, 2.0 g/L $MgSO_4$*$7H_2O$, 0.2 g/L $CaCl_2$*$2H_2O$, 0.33 g/L ferric ammonium citrate, 0.5 g/L yeast extract, 0.1 mg/L vitamin B12, 1.0 mg/L FeSO4*7H2O, 1 mg/L ZnSO4*7H2O, 0.1 g/L CuSO4*5H2O, 1 mg/L CoCl2*6H2O, 0.3 mg/L MnSO4*7H2O, 0.1 g/L H3BO4, 0.10 g/L NaMoO4*2H2O, 10 mg/L NaCl with the final pH adjusted to 6.8. Cultures were started from frozen stocks (15% glycerol as cryoprotectant) in 50 mL of medium in a 250 mL baffled flask. The cultures were incubated at 34° C. and 300 rpm shaking for 24 hours. The amount of 1,3-propanediol produced was measured by HPLC under the following conditions:

Column: Showdex SH1011
Sample volume: 20 μL
Mobile phase: 0.01 N H2SO4
Flow rate: 0.5 ml/min
Column temperature 50° C.
Detector: Waters 996 photodiode array
Detector temperature: 40° C.
Run time: 40 min Results are shown in Table 9 below. Products from glucose fermentation by the RJ8n pBE93-k1 strain of *E. coli* include glycerol (an intermediate metabolite) and 1,3-propanediol. Experiments were conducted in duplicate flasks and assayed at 24 hr. In this system, glucose in the hydrolysate was converted to both glycerol and 1,3-propanediol.

TABLE 9

Substrate utilization and product formation by fermentation with *E. coli*.

|  | Broth at time zero | Flask 1, 24 hr | Flask 2, 24 hr |
|---|---|---|---|
| Glucose (g/L) | 7.39 | 2.12 | 2.10 |
| Glycerol (g/L) | 0 | 3.14 | 3.14 |
| 1,3-propanediol (g/L) | 0 | 1.03 | 1.07 |
| Glucose use | 0 | 71% | 72% |

Example 11

Formation of Acetamide During Pretreatment

Samples derived from cobs pretreated according to the processes described in Example 3 and Example 4 were analyzed to determine the fate of the acetyl groups in the biomass. The pretreatment liquors (pretreatment mixture with insoluble solids removed) were assayed for acetic acid and acetamide content as follows. The pH of each sample was adjusted to about 3 with $H_2SO_4$ (72%). For measurement of acetamide, the sample was passed through a 0.2 μm filter and analyzed by HPLC according to the conditions listed below. For measurement of total acetate (includes acetate present as acetic acid and acetamide), the acidified sample was autoclaved for 1 hr at 121° C.; acetamide was quantitatively converted to acetic acid during this step. After autoclaving, the sample was allowed to cool. The sample was then passed through a 0.2 μm filter into a sample vial and analyzed according to the conditions listed below. Acetic acid and acetamide concentrations were determined from standard curves generated for each.

Mobile phase: 0.01 N $H_2SO_4$, 0.2 μm filtered and degassed
Flow rate: 0.6 mL/min
Column temperature: 55-65° C.
Detector temperature: As close to column temperature as possible
Detector: Refractive index
Run time: 60 min
Column: Biorad Aminex HPX-87H column with corresponding guard column Results for the 3 different pretreatment conditions assayed are shown in Table 10. In each case, all of the acetyl groups were solubilized to either acetic acid or acetamide.

TABLE 10

Conversion of acetyl groups in biomass to acetamide during pretreatment.

| Feedstock | Pretreat time (hr) | Pretreat temp (° C.) | Ammonia (g/100 g DWB) | DWB (Pretreat) | Fraction of initial acetyl recovered in liquor | Fraction of recovered acetyl as acetamide | Fraction of recovered acetyl as acetic acid |
|---|---|---|---|---|---|---|---|
| Whole cob | 8 hr | 93 | 6 | 40% | 100% | 44% | 56% |
| Fractured cob | 4 hr | 85 | 2 | 30% | 90% | 10% | 90% |
| Fractured cob | 20 min | 145 | 2 | 30% | 99% | 9% | 91% |

DWB, dry weight of biomass. (percent is calculated relative to the total weight of the biomass-aqueous ammonia mixture)

Using an ammonia concentration of 6%, nearly half of the acetyl groups were converted to acetamide, which is non-inhibitory for biocatalyst growth as shown in Example 12.

Example 12

Effect of Acetamide and Acetic acid on *Zymomonas* Growth

To test the toxicity of acetamide and acetic acid, *Z. mobilis* strain 8b (described in Example 9) was grown in fermentation medium at pH 6.0 with and without acetamide or acetic acid. Fermentation medium was composed of 10 g/L yeast extract, 2 g/L $KH_2PO_4$, 70 g/L glucose, 40 g/L xylose and 0.1 M MES buffer. *Z. mobilis* 8b was grown in 25-mL baffled Erlenmeyer shake flasks rotating at 150 rpm at 30° C. in unsupplemented medium (control), medium supplemented with 6 g/L acetamide, or medium supplemented with 7.2 g/L acetic acid. As shown in FIG. 1, the presence of acetamide had no influence on the growth rate or final density of *Z. mobilis*, whereas the presence of acetic acid resulted in a reduced growth rate and lower cell yield (as measured by dry cell mass).

Example 13

Pretreatment of Bagasse at High Biomass Concentration, High Temperature, and Very Low Ammonia, and Saccharification at Low and High Concentration The PEHReactor (described in General Methods), with no attrition media, was charged with 1.27 cm-milled bagasse (370 g, dry weight basis). This sugar cane bagasse was NIST Reference Material RM8491, from sugar cane clone H65-7052, originally obtained from the Hawaii Sugar Planters Association, Kunia substation, Oahu, Hi. It was milled in a Wiley mill to pass through a 2 mm screen, with the fines (+74 mesh) removed. The PEHReactor vessel was cooled to 4° C. by rotation in contact with ice on the outer surface. A vacuum was applied to the reactor vessel, and dilute ammonium hydroxide solution, that was pre-cooled in a cold room at 4° C. and passed through tubing immersed in an ice-water bath, was injected to give an ammonia concentration of 4 g/100 g dry weight of biomass and a dry weight of biomass concentration of 45 g/100 g total biomass-aqueous ammonia mixture. The reactor vessel charged with ammonia and bagasse was cooled to 4° C. by applying ice to the surface of the rotating reactor vessel, and rotated at 4° C. for 30 min. At this time the contents were transferred to the steam gun reactor that is described in General Methods. Once the steam gun reactor was charged with the ammonia-bagasse mixture, the temperature was increased to 145° C. and the mixture was held at temperature for 20 minutes. At the end of the pretreatment time, the bagasse was discharged from the steam gun reactor through a 1-in circular die into a flash tank. A sample of pretreated bagasse was subsequently saccharified in a shake flask and another sample (approximately 163 g dry weight) was saccharified in the PEHReactor. The shake flask saccharification was carried out at 5% dry weight of biomass relative to the total weight of the pretreated biomass-saccharification enzyme consortium mixture, while the PEHReactor saccharification was carried out at 30% dry weight of biomass relative to the total weight of the pretreated biomass-saccharification enzyme consortium mixture. The temperature was maintained at 50° C.

For the PEHReactor saccharification, about 476 g (~163 g dry weight) pretreated biomass and 22 ceramic attrition cylinders were added to the reactor vessel. The pH was adjusted to 5.0-5.5 with solid citric acid. The reactor vessel was kept inside an incubator chamber controlled to 50° C. and rotated axially at 19 rpm. Unpretreated bagasse was also saccharified at 5% dry weight of biomass relative to the total weight of the pretreated biomass-saccharification enzyme consortium mixture in a shake flask. All saccharifications were done with 28.4 mg/g cellulose Spezyme CP® cellulase and 28.4 mg/g cellulose Multifect® xylanase at 50° C. and pH 5.5 for 96 hr. Yields given in Table 11 below are the release as percent of theoretical yield.

TABLE 11

Yields following pretreatment and saccharification of bagasse.

|  | No pretreatment 5% saccharification | Pretreated 5% DWB saccharification | Pretreated 30% DWB saccharification |
| --- | --- | --- | --- |
| Monomer glucose | 0.5% | 16.6% | 23.3% |
| Total glucose | ND | ND | 36.4% |
| Monomer xylose | 1.3% | 15.6% | 17.2% |
| Total xylose | ND | ND | 37.4% |

ND: not determined

The results demonstrate that pretreatment of bagasse with very low ammonia allows substantial sugar release as compared to the unpretreated control, and that saccharification at high dry biomass concentration in the PEHReactor is very effective in releasing sugars.

Example 14

Pretreatment of Yellow Poplar Sawdust at High Biomass Concentration, High Temperature, and Very Low Ammonia, and Saccharification at Low and High Concentration The PEHReactor, without attrition media, was charged with yellow poplar sawdust (596 g, dry weight basis; purchased from Sawmiller Inc., Haydenville, Ohio). A vacuum was applied to the reactor vessel, and dilute ammonium hydroxide solution was injected to give an ammonia concentration of 6 g/100 g dry weight of biomass and a dry weight of biomass concentration of 44 g/100 g total biomass-aqueous ammonia mixture. The reactor vessel charged with ammonia and yellow poplar sawdust was brought to 4° C. as described in Example 13, and rotated at 4° C. for 30 min. At this time the contents were transferred to the steam gun reactor. Once the steam gun reactor was charged with the ammonia-poplar mixture, the temperature was increased to 145° C. and the mixture was held at temperature for 20 minutes. At the end of the pretreatment time, the yellow poplar sawdust was discharged from the steam gun reactor through a 1-in circular die into a flash tank. A sample of pretreated yellow poplar sawdust was subsequently saccharified as described in Example 13 in a shake flask, and another sample was saccharified in the PEHReactor. The shake flask saccharification was carried out at 5% dry weight of biomass relative to the total weight of the pretreated biomass-saccharification enzyme consortium mixture, while the PEHReactor saccharification (using ~279 g dry weight pretreated sawdust) was carried out at 30% dry weight of biomass relative to the total weight of the pretreated biomass-saccharification enzyme consortium mixture. Unpretreated yellow poplar sawdust was also saccharified at 5% dry weight of biomass relative to the total weight of the pretreated biomass-saccharification enzyme consortium mixture in a shake flask. All saccharifications were done with 28.4 mg/g cellulose Spezyme CP® cellulase and 28.4 mg/g cellulose Multifect® xylanase at 50° C. and pH 5.5 for 96 hr. Yields given in Table 12 below are the release or each sugar as a percentage of theoretical yield.

TABLE 12

Yields following pretreatment and saccharification of yellow poplar sawdust.

| Component | No pretreatment 5% DWB saccharification | Pretreated 5% DWB saccharification | Pretreated 30% DWB saccharification |
|---|---|---|---|
| Monomer glucose | 2.7% | 11.1% | 20.6% |
| Total glucose | ND | ND | 30.0% |
| Monomer xylose | 0% | 17.9% | 18.9% |
| Total xylose | ND | ND | 40.2% |

ND: not determined

The results demonstrate that pretreatment of yellow poplar sawdust with very low ammonia allows substantial sugar release as compared to the unpretreated control, and that saccharification at high dry weight of biomass in the PEHReactor is more effective in releasing sugars than the shake flask.

Example 15

Ethanol Production by Yeast Fermentation on Hydrolyzate from Very Low Ammonia-Pretreated and Saccharified Cob Biomass The same hydrolyzate used to produce 1,3-propanediol in Example 10 was also used to produce ethanol by yeast fermentation. This hydrolyzate was used as a source of fermentable sugar for conversion to ethanol by wild-type *Saccharomyces cerevisiae* in shake flasks. The hydrolyzate was used at 10% (v/v) strength, with the balance being aqueous medium consisting of 10 g/L yeast extract, and 20 g/L peptone. Yeast were cultured in 50 mL of medium in a 250 mL baffled flask. The cultures were incubated at 30° C. with 250 rpm shaking for 24 hours. The amount of ethanol produced was measured by HPLC as described in Example 9, and results from duplicate flasks are listed in Table 13 below.

TABLE 13

Substrate utilization and product formation by fermentation with yeast.

| | Broth at time zero | Flask 1, 24 hr | Flask 2, 24 hr |
|---|---|---|---|
| Glucose (g/L) | 13.9 | 1.3 | 0.9 |
| Ethanol (g/L) | 0 | 4.1 | 4.3 |
| Glucose use | 0 | 91% | 94% |

Example 16

Lactic Acid Production by Lactobacillus Fermentation on Hydrolyzate from Very Low Ammonia-Pretreated and Saccharified Cob Biomass The same hydrolyzate used to produce 1,3-propanediol in Example 10 was also used to produce lactic acid by fermentation with *Lactobacillus brevis* in shake flasks. The hydrolyzate was used at 10% (v/v), with the balance being aqueous medium consisting of 5 g/L yeast extract, 10 g/L peptone, 2 g/L ammonium citrate, 5 g/L sodium acetate, 0.1 g/L $MgSO_4$, 0.05 g/L $MnSO_4$ and 2 g/L $K_2HPO_4$ and 1 g/L Tween. The *Lactobacillus* was cultured in 50 mL broth in 250 mL baffled flasks. Duplicate cultures were incubated at 34° C. with 150 rpm shaking for 24 hours. The amount of lactic acid produced was measured by HPLC as described in Example 10 and is listed in Table 14. The two Flask 2 samples are duplicate assays of the same culture.

TABLE 14

Substrate utilization and product formation by fermentation with *Lactobacillus brevis*

| | Broth at time zero | Flask 1, 24 hr | Flask 2, 24 hr | Flask 2, 24 hr |
|---|---|---|---|---|
| Glucose (g/L) | 25.1 | 4.6 | 3.9 | 3.3 |
| Lactic acid (g/L) | 0 | 8.8 | 6.2 | 6.4 |
| Glucose use | 0 | 82% | 84% | 87% |

Example 17

Cob Pretreatment at Higher Dry Biomass Concentration with Very Low Ammonia

Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen. Approximately 805 g fractured cobs were loaded into the PEHReactor. Moisture content in the cobs was approximately 7%. The atmosphere in the reactor vessel was flushed 5 times with nitrogen prior to loading. The reactor, with no attrition media, was preheated to 75° C. before the start of the experiment, without rotation. When the temperature within the reactor vessel stabilized at 75° C. the rolling mechanism in the incubator was turned on and the rotation adjusted to 19 rpm. The appropriate amount of dilute ammonium hydroxide solution to give an ammonia concentration of 6 g ammonia/100 g dry weight of biomass and a solids concentration of 50 g dry weight of biomass/100 g total weight of biomass-ammonia mixture was then pumped into the reactor. Ethanol at 1 g/100 g dry weight of biomass was also added to the solution. The ammonia solution was pumped through a heated loop in a water bath heated to ~75° C., fabricated using a 2-gal Parr reactor. The heated dilute ammonium hydroxide solution was injected via an injection lance into the reactor vessel and sprayed on the fractured cobs rotating and tumbling in the reactor. The reactor was maintained at 75° C. for 2 hr while turning at 19 rpm. At the end of that time, a vacuum (approximately 85 kPa) was applied to the reactor vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure $CO_2$ and held at pressure for 30 min at 50° C.

Following this, the reactor was depressurized, opened and attrition media were added. The pH of the contents was adjusted to approximately 5.5 by injecting 1 M citric acid buffer at pH 4.8 using the injection lance, to increase the citric acid buffer strength to ~75 mM, plus adding citric acid monohydrate. Not all of the ammonia was stripped off in the vacuum step nor neutralized with $CO_2$. The citric acid buffer was injected into the reactor following heating to 50° C. and then the contents was allowed to equilibrate by incubating the reactor at 50° C. and 19 rpm for 1 hour. Injection of the citric acid buffer while rotating the reactor using the injection lance allowed for a more even spraying and distribution of the buffer on the pretreated cob particles. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 12.9 mg/g cellulose Spezyme CP (Genencor) and 5 mg active protein/g cellulose enzyme consortium consisting of β-glucosidase, xylanase, β-xylosidase and arabinofuranosidase were loaded into the reactor. The reactor remained in the incubator at 50° C. and 19 rpm for 72 hr. Following this pretreatment and saccharification, monomer glucose yield was 62.0% and monomer xylose yield was 31.0%. Total glucose yield was 75.2% and total xylose was 80.3%.

Example 18

Cob Pretreatment at Higher Solids Concentration with Very Low Ammonia and Alternate Conditions Whole corn cobs were processed with a hammermill (10-inch hammer mill, Glen Mills Inc., Clifton, N.H.) to pass through a 1.27 cm screen. Approximately 805 g fractured cobs were loaded into the PEHReactor. Moisture content in the cobs was approximately 7%. Twenty-two ceramic attrition cylinders (3.2 cm diameter×3.2 cm long; E. R. Advanced Ceramics, East Palestine, Ohio) were also added to the reactor. The reactor was preheated to 95° C. before the start of the experiment, without rotation. A vacuum (approximately 85 kPa) was applied to the reactor vessel before the start and the vessel was sealed off. When the temperature within the reactor vessel stabilized at 95° C. the rolling mechanism in the incubator was turned on and the rotation adjusted to 19 rpm. The appropriate amount of dilute ammonium hydroxide solution to give an ammonia concentration of 6 g ammonia/100 g dry weight of biomass and a solids concentration of 50 g dry weight of biomass/100 g total weight of biomass-ammonia mixture was then pumped into the reactor. The ammonia solution was pumped through a heated loop in a boiling water bath fabricated using a 2-gal Parr reactor. The heated dilute ammonium hydroxide solution was injected via an injection lance into the reactor vessel and sprayed on the fractured cobs rotating and tumbling in the reactor. The reactor was maintained at 95° C. for 2 hr while turning at 19 rpm. At the end of that time, a vacuum (approximately 85 kPa) was applied to the reactor vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure and held at pressure for 30 min at 500° C.

Following this, the reactor was depressurized, opened and the pH of the contents was adjusted to approximately 5.5 by injecting 1 M citric acid buffer, pH 4.8, into which citric acid monohydrate was added and dissolved. The citric acid buffer was injected into the reactor following heating to 50° C. and then the contents was allowed to equilibrate by incubating the reactor at 50° C. and 19 rpm for 1 hour. Injection of the citric acid buffer while rotating the reactor using the injection lance allowed for a more even spraying and distribution of the buffer on the pretreated cob particles. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 12.9 mg/g cellulose Spezyme CP (Genencor) and 5 mg active protein/g cellulose enzyme consortium consisting of β-glucosidase, xylanase, β-xylosidase and arabinofuranosidase were loaded into the reactor. The reactor remained in the incubator at 50° C. and 19 rpm for 72 hr. Following this pretreatment and saccharification, monomer glucose yield was 50.7% and monomer xylose yield was 35.7%. Total glucose and xylose yields were 71.7% and 89.8%, respectively.

Example 19

Pretreatment of Cobs with Very Low Ammonia and Additional Base

Whole corn cobs were processed with a jaw crusher (2.2 kW motor) with a jaw spacing of approximately 0.95 cm, followed by a delumper (1.5 kW motor, Franklin Miller Inc.), followed by screening with a Sweco screen equipped with a 1.9 cm U.S. Standard screen. Approximately 460 g fractured cobs were loaded into the PEHReactor. Moisture content in the cobs was approximately 7%. The reactor was preheated to 95° C. before the start of the experiment, without rotation. A vacuum (approximately 85 kPa) was applied to the reactor vessel before the start and the vessel was sealed off. When the temperature within the vessel re-stabilized at 95° C. the rolling mechanism in the incubator was turned on and the rotation was adjusted to 19 rpm. The appropriate amount of ammonium hydroxide solution to give an ammonia concentration of 3.2 g ammonia/100 g dry weight of biomass and NaOH to give a concentration of 1.9 g NaOH/100 g dry weight of biomass while maintaining a solids concentration of 30 g dry weight of biomass/100 g total weight of biomass-ammonia mixture was then pumped into the reactor. The ammonia and additional base solution was pumped through a heated loop in a boiling water bath fabricated using a 2-gal Parr reactor. The heated dilute ammonium hydroxide solution was injected via an injection lance into the reactor vessel and sprayed on the fractured cobs rotating and tumbling in the reactor. Following injection, the vacuum on the vessel was relieved to atmospheric pressure. The reactor was maintained at 95° C. 30 min, then the temperature was lowered to 85° C. where it was maintained for 4 hr. At the end of that time, a vacuum (approximately 85 kPa) was applied to the reactor vessel for 30 minutes to remove ammonia and drop the temperature of the contents of the reactor to approximately 50° C. Carbon dioxide was then injected into the reactor to relieve the vacuum and the reactor was pressurized to 103 kPa gauge pressure and held at pressure for 30 min at 50° C.

Following this, the reactor was depressurized, opened and the pH of the contents was adjusted to approximately 5.5 by injecting approximately 75 ml of 1 M citric acid buffer, pH 4.8, into which citric acid monohydrate was added and dissolved. The citric acid buffer was injected into the reactor following heating to 50° C. and the contents was then allowed to equilibrate by incubating the reactor at 50° C. and 19 rpm for 1 hour. Injection of the citric acid buffer while rotating the reactor using the injection lance allowed for a more even spraying and distribution of the buffer on the pretreated cob particles. The reactor was removed from the incubator, opened, and the pH of a sample determined. If the pH was above 5.5, then additional solid citric acid monohydrate was added and the reactor was incubated with mixing at 50° C. for an additional hour. This process was repeated until the pH was approximately 5.5. Once the desired pH was reached, 28.4 mg/g cellulose Spezyme CP (Genencor) and 28.4 mg/g cellulose Multifect were loaded into the reactor. The reactor remained in the incubator at 50° C. and 19 rpm for 72 hr. Following this pretreatment and saccharification, monomer glucose yield was 56.1% and monomer xylose yield was 39.5%. Total glucose and xylose yields were 82.8% and 84.2%, respectively. These values are the averages of 2 experiments.

Example 20

Room Temperature and Very Low Ammonia Pretreatment

Whole corn cobs were processed with a jaw crusher (2.2 kW motor) with a jaw spacing of approximately ⅜ inch, followed by a delumper (1.5 kW motor, Franklin Miller Inc.), followed by screening with a Sweco screen equipped with a 1.9 cm U.S. Standard screen. Approximately 460 g fractured cobs were loaded into the PEHReactor. Moisture content in the cobs was approximately 7%. Twenty-two ceramic attrition cylinders (3.2 cm diameter×3.2 cm long; E. R. Advanced Ceramics, East Palestine, Ohio) were also added to the reactor. A vacuum (approximately 85 kPa) was applied to the reactor vessel before the start and the vessel was sealed off. When the temperature within the reactor re-stabilized at room temperature (22-26° C.) the rolling mechanism in the incubator was turned on and rotation was adjusted to 19 rpm. The appropriate amount of dilute ammonium hydroxide solution to give an ammonia concentration of 4 g ammonia/100 g dry weight of biomass and while maintaining a solids concentration of 30 g dry weight of biomass/total weight of biomass-ammonia mixture was then pumped into the reactor. The dilute ammonium hydroxide solution was injected via an injection lance into the reacter vessel and sprayed on the fractured cobs rotating and tumbling in the reactor. Following injection, the vacuum on each vessel was relieved to atmospheric pressure. The reactor was maintained at room temperature (22-26° C.) for 24 hr. At the end of that time, a vacuum (approximately 81 kPa) was applied to the reaction vessel for 30 minutes to remove ammonia. Carbon dioxide was then injected into the reactor to relieve the vacuum and the reactor was pressurized to 103 kPa gauge pressure with $CO_2$ and held at pressure for 30 min at room temperature.

Following this, the reactor was depressurized, opened and the pH of the contents was adjusted to approximately 5.5 by adding citric acid monohydrate following heating to 50° C., and then allowed to equilibrate by incubating the reactor at 50° C. and 19 rpm. The reactor was removed from the incubator, opened, and the pH of a sample determined. If the pH was above 5.5, then additional solid citric acid monohydrate was added and the reactor was incubated with mixing at 50° C. This process was repeated until the pH was approximately 5.5. Once the desired pH was reached, 12.9 mg/g cellulose Spezyme CP (Genencor) and 5 mg active protein/g cellulose enzyme consortium consisting of β-glucosidase, xylanase, β-xylosidase and arabinofuranosidase were loaded into the reactor. The reactor remained in the incubator at 50° C. and 19 rpm for 72 hr. Following this pretreatment and saccharification, monomer glucose yield was 41.7% and the monomer xylose yield was 25.4%. Total glucose and xylose yields were 50.1% and 53.2%, respectively. These values were the averages of 2 experiments.

What is claimed is:

1. A method for producing a target chemical derivable from biomass comprising:
   a) for a period of time up to about 25 hours, contacting biomass with an aqueous solution comprising ammonia, wherein the ammonia is present at a concentration at least sufficient to maintain alkaline pH of the biomass-aqueous ammonia mixture but wherein said ammonia is present at 12 or less weight percent relative to dry weight of biomass, and further wherein the dry weight of biomass is at a solids concentration of at least about 15 weight percent relative to the weight of the biomass-aqueous ammonia mixture;
   b) contacting the product of step (a) with a saccharification enzyme consortium comprising one or more hemicellulose-hydrolyzing glycosidase, under suitable conditions to produce fermentable sugars wherein said fermentable sugars provide a carbohydrate source for a biocatalyst for a fermentation process; and
   c) contacting the product of step (b) with at least one biocatalyst able to ferment the sugars to produce the target chemical under suitable fermentation conditions.

2. The method of claim 1 wherein steps (b) and (c) are performed concurrently.

3. The target chemical of claim 1 selected from the group consisting of acids, alcohols, alkanes, alkenes, aromatics, aldehydes, ketones, biopolymers, proteins, peptides, amino acids, vitamins, antibiotics, and pharmaceuticals.

4. The method of claim 1, wherein the target chemical is selected from the group consisting of methanol, ethanol, propanol, isopropanol, butanol, ethylene glycol, propanediol, butanediol, glycerol, erythritol, xylitol, sorbitol, acetic acid, lactic acid, propionic acid, 3-hydroxypropionic acid, butyric acid, gluconic acid, itaconic acid, citric acid, succinic acid, levulinic acid, glutamic acid, aspartic acid, methionine, lysine, glycine, arginine, threonine, phenylalanine, tyrosine, methane, ethylene, acetone, and industrial enzymes.

5. The method of claim 4, wherein the target chemical is lactic acid, propanediol, or ethanol.

6. The method of claim 1 wherein said at least one biocatalyst is selected from the group consisting of bacteria, filamentous fungi and yeast.

7. The method of claim 1 wherein said at least one biocatalyst is selected from the group consisting of wild type, mutant, or recombinant *Escherichia, Zymomonas, Candida, Saccaromyces, Pichia, Streptomyces, Bacillus, Lactobacillus* and *Clostridium*.

8. The method of claim 1 wherein said at least one biocatalyst is selected from the group consisting of recombinant *Escherichia coli, Zymomonas mobilis, Bacillus stearothermophilus, Saccharomyces cerevisiae, Clostridia thermocellum, Thermoanaerobacterium saccharolyticum*, and *Pichia stipitis*.

9. The method of claim 1 wherein the pH of the biomass-aqueous ammonia mixture is greater than 8.

10. The method of claim 1 wherein vacuum is applied to the biomass prior to contacting the biomass with an aqueous solution comprising ammonia.

11. The method of claim 1 wherein said dry weight of biomass is at a solids concentration of from at least about 15% to about 80%.

12. The method of claim 11 wherein said dry weight of biomass is at a solids concentration of from at least about 15% to about 60%.

13. The method of claim 1 wherein said ammonia is present at less than about 10 weight percent relative to dry weight of biomass.

14. The method of claim 13 wherein said ammonia is present at about 6% or less weight percent relative to dry weight of biomass.

15. The method of claim 1 wherein biomass is selected from the group consisting of bioenergy crops, agricultural residues, municipal solid waste, industrial solid waste, yard waste, wood and forestry waste.

16. The method of claim 1 wherein biomass is selected from the group consisting of switchgrass, waste paper, sludge from paper manufacture, corn grain, corn cobs, corn husks, corn stover, grasses, wheat, wheat straw, hay, barley, barley straw, rice straw, sugar cane bagasse, sorghum, soy, components obtained from processing of grains, trees, branches, roots, leaves, wood chips, sawdust, shrubs and bushes, vegetables, fruits, flowers and animal manure.

17. The method of claim 16 wherein biomass is selected from the group consisting of corn cobs, corn stover, corn husks, sugar cane bagasse, sawdust, switchgrass, wheat straw, hay, barley straw, rice straw, and grasses.

18. The method of claim 17 wherein biomass is selected from the group consisting of corn cobs, corn stover, sawdust, and sugar cane bagasse.

19. The method of claim 1 wherein ammonia selected from the group consisting of ammonia gas, ammonium hydroxide, urea, and combinations thereof.

20. The method of claim 1 wherein (a) is carried out at a temperature of from about 4° C. to about 200° C.

21. The method of claim 20 wherein (a) is carried out at a temperature of from about 75° C. to about 150° C.

22. The method of claim 21 wherein (a) is carried out at a temperature of from greater than 90° C. to about 150° C.

23. The method of claim 1 wherein (a) is carried out for a period of time of up to about 8 hours.

24. The method of claim 1 or claim 2 wherein at least a portion of the ammonia of (a) is removed prior to (b).

25. The method of claim 24 wherein ammonia from (a) is recycled.

26. The method of claim 1 wherein (a), (b) or (a) and (b) are repeated at least one time.

27. The method of claim 1 further comprising adding at least one plasticizer, softening agent or combination thereof in (a).

28. The method of claim 27 wherein said at least one plasticizer, softening agent or combination thereof is selected from the group consisting of polyols, esters of polyols, glycol ethers, acetamide, ethanol, and ethanolamines.

29. The method of claim 1 further comprising applying energy for reducing the size of the biomass during (a), before or during (b), or a combination thereof.

30. The method of claim 29 wherein said energy is selected from the group consisting of milling, crushing, grinding, shredding, chopping, disk refining, ultrasound and microwave.

31. The method of claim 1, wherein carbon dioxide from fermentation is used to adjust the pH of the pretreatment mixture prior to saccharification.

32. The method of claim 1 wherein said saccharification enzyme consortium comprises at least one glycosidase.

33. The method of claim 1 wherein said saccharification enzyme consortium further comprises at least one additional enzyme selected from the group consisting of cellulose-hydrolyzing glycosidases, starch-hydrolyzing glycosidases, peptidases, lipases, ligninases and feruloyl esterases.

34. The method of claim 1 wherein said saccharification enzyme consortium comprises at least two enzymes selected from the group consisting of cellulases, endoglucanases, exoglucanases, cellobiohydrolases, "β-glucosidases", xylanases, endoxylanases, exoxylanases, β-xylosidases, arabinoxylanases, mannases, galactases, pectinases, glucuronidases, amylases, α-amylases, β-amylases, glucoamylases, α-glucosidases and isoamylases.

35. The method of claim 1 wherein (b) is performed at a temperature of from about 15° C. to about 100° C. and at a pH of from about 2 to about 11.

* * * * *